US011780833B2

(12) United States Patent
Bakare et al.

(10) Patent No.: US 11,780,833 B2
(45) **Date of Patent: *Oct. 10, 2023**

(54) EMETINE DERIVATIVES, PRODRUGS CONTAINING SAME, AND METHODS OF TREATING CONDITIONS USING SAME

(71) Applicant: HOWARD UNIVERSITY, Washington, DC (US)

(72) Inventors: Oladapo Bakare, Silver Spring, MD (US); Samuel Ray Denmeade, Ellicott City, MD (US); Emmanuel S. Akinboye, Columbia, MD (US)

(73) Assignee: HOWARD UNIVERSITY, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/045,254

(22) Filed: Jul. 25, 2018

(65) Prior Publication Data

US 2019/0016716 A1 Jan. 17, 2019

Related U.S. Application Data

(63) Continuation of application No. 15/352,290, filed on Nov. 15, 2016, now abandoned, which is a continuation of application No. 13/828,877, filed on Mar. 14, 2013, now Pat. No. 9,492,560, which is a continuation of application No. PCT/US2012/038655, filed on May 18, 2012.

(60) Provisional application No. 61/488,601, filed on May 20, 2011.

(51) Int. Cl.

| | |
|---|---|
| ***C07K 7/06*** | (2006.01) |
| ***C07D 455/08*** | (2006.01) |
| ***C07D 401/06*** | (2006.01) |

(52) U.S. Cl.

CPC ......... *C07D 455/08* (2013.01); *C07D 401/06* (2013.01); *C07K 7/06* (2013.01)

(58) Field of Classification Search

None

See application file for complete search history.

(56) References Cited

U.S. PATENT DOCUMENTS

| | | | | |
|---|---|---|---|---|
| 3,856,795 | A * | 12/1974 | Yardley | C07C 209/64 544/358 |
| 6,030,997 | A | 2/2000 | Eilat | |
| 7,744,861 | B2 | 6/2010 | Zhao | |
| 7,893,023 | B2 | 2/2011 | Trouel | |
| 7,906,477 | B2 | 3/2011 | Denmeade | |
| 7,910,553 | B2 | 3/2011 | Mitra | |
| 7,932,294 | B2 | 4/2011 | Satyam | |
| 8,124,051 | B2 * | 2/2012 | Minko | A61K 47/62 424/1.45 |
| 9,492,560 | B2 * | 11/2016 | Bakare | C07D 455/08 |
| 2004/0059138 | A1 | 3/2004 | Schreiber et al. | |
| 2009/0062222 | A1 | 3/2009 | Sherman et al. | |

FOREIGN PATENT DOCUMENTS

| | | |
|---|---|---|
| EP | 0 338 372 A2 | 10/1989 |
| GB | 1 274 199 | 5/1972 |

OTHER PUBLICATIONS

PCT International Preliminary Report on Patentability of the International Searching Authority dated Nov. 28, 2013 for International Appln No. PCT/US2012/038655, 6 pages.

PCT International Search Report of the International Searching Authority dated Oct. 4, 2012 for International Appln No. PCT/US2012/038655, 3 pages.

Akinboye, Emmaneul S., et al., Cytotoxic activities of a twelve-member library of emetine dithiocarbamate ester analogs on androgen-independent PCS and DU145 prostate cancer cell lines, Abstracts of Papers, 239th ACS National Meeting, San Francisco, California, United States, Mar. 21-25, 2010, MEDI-390, 1 page.

Akinboye, Emmaneul S., et al., Cytotoxicity studies of selected emetine dithiocarbamate ester derivatives in androgen-positive prostate cancer LNCaP cells, Abstract accepted for Middle Atlantic Regional Meeting of the American Chemical Society, Maryland, United States, May 2011 1 page.

Akinboye, Emmaneul S., et al., Solution phase parallel synthesis of dithiocarbamate ester analogs of emetine as potential anticancer agents, Abstracts of Papers, 238th ACS National Meeting, Washington, District of Columbia, United States, Aug. 16-20, 2009, MEDI-278, 1 page.

Akinboye, Emmanuel S., et al., Poster for the ACS Meeting, Fall 2009, Solution Phase Parallel Synthesis of Dithiocarbamate Ester Analogs of Emetine as Potential Anticancer Agents, 1 page.

Akinboye, Emmanuel S., et al., Poster for the ACS Meeting, Spring 2010, Cytotoxic Activities of a twelve-member library of emetine dithiocarbamate ester analogs on androgen-independent PC3 and DU145 prostate cancer cell lines, 1 page.

Bakare, Oladapo, et al., Synthesis and MEK1 Inhibitory Activities of Imido-Substituted 2-Chloro-1,4-naphthoquinones, Bioorganic & Medicinal Chemistry, 2003, vol. 11, pp. 3165-3170.

Berhe, Solomon, et al., Microwave-Assisted Synthesis of Imido-Substituted 2-Chloro-1,4-naphthoquinone Derivatives and their Cytotoxic Activities on Three Human Prostate Cancer Cell Lines, Letters in Drug Design & Discovery, 2008, vol. 5, pp. 485-488.

(Continued)

*Primary Examiner* — Maury A Audet

(74) *Attorney, Agent, or Firm* — Sughrue Mion, PLLC

(57) ABSTRACT

Compounds are provided herein which are emetine derivatives that can be used as prodrugs which selectively undergo activation to release emetine in specific cellular conditions. In one aspect, a blocking group is incorporated onto the emetine molecule by the derivization of the N2'-position with moieties that can be selectively removed by hydrolysis in the cancer/tumor microenvironment. Such compounds are less cytotoxic than emetine and are substantially inactive in non-cancerous cells. In one aspect, the compounds described herein can be used for the treatment of metastatic and non-metastatic cancers, including, for example, breast cancer, prostate cancer, lung cancer, and leukemia.

8 Claims, 4 Drawing Sheets

Specification includes a Sequence Listing.

(56) References Cited

OTHER PUBLICATIONS

Brossi, et al., Syntheses in the emetine series. V. A new total synthesis of emetine. Helvetica Chimica Acta (1959), 42, pp. 1515-1522.
Brossi, et al., Synthesis in the emetine series. VIII. dl-Emetine isomers of the 2,3-cis series. Helvetica Chimica Acta (1962), 45, pp. 1899-1907.
Dimitrijevic, Sasa, etal., Synthesis and Characterization of N-(2-Hydroxypropyl)-Methacrylamide (HPMA) Copolymer-Emetine Conjugates, Journal of Bioactive and Compatible Polymers, Jul. 1998, vol. 13, No. 3, pp. 165-178, [online], [retrieved on May 12, 2014]. Retrieved from the Internet: <URL: http://jbc.sagepub.eom/content/13/3/165.short>, Abstract only, 1 page.
Extended European Search Report, European Patent Application No. 12789195, dated Feb. 11, 2015, 9 pages.
Frei, et al. Liquid chromatography of dansyl derivatives of some alkaloids and the application to the analysis of pharmaceuticals. Journal of Chromatography (1976), 116(2), 365-77 (abstract only).
Gradnik, B., etal., Amebicides. I—Emetine Derivatives. Journal of Medicinal Chemistry, vol. 14 No. 3, 1971, pp. 255-256.
Grollman, Arthur R, Structural Basis for Inhibition of Protein Synthesis by Emetine and Cycloheximide Based on an Analogy Between Ipecac Alkaloids and Glutarimide Antibiotics, Biochemistry, Proc. N. A. S., Sep. 22, 1966, pp. 1867-1874.
Grussner, et al. Syntheses in the emetine series. VI. Another synthesis. Helvetica Chimica Acta (1959), 42, pp. 2431-2439.
Nacken, M., et al., Aminoacylierungen des Emetins. Archiv Der Pharmazie, vol. 303, No. 2, Jan. 1, 1971, pp. 122-133.
Pakrashi, et al. Studies on Indian medicinal plants. XIX. Alangamide, a new alkaloid from the seeds of Alangium lamarckii. Indian Journal of Chemistry (1969), 7(6), 635-6 (abstract only).
Pettit, George R., et al., Synthesis of 2'-(N,-bis(2-chloroethyl)glycyltryptophyl)emetine and related peptides. Canadian Journal of Chemistry, vol. 45, No. 13, 1967, pp. 1561-1566.
Salamink, et al. Muscaridine. II. Recueil des Travaux Chimiques des Pays-Bas et de la Belgique (1960), 79, pp. 485-487.
Yardley, J.P., et al., Synthesis and Amebicidal Activities of Some 1', 2'-Secoemetine Derivatives. Journal of Medicinal Chemistry, vol. 10, No. 6, 1967, pp. 1088-1091.

* cited by examiner

SEQUENCE LISTING

<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Protein sequence is a substrate for hydrolysis by Prostate Specific Antigen (PSA)

<400> SEQUENCE: 1

His Ser Ser Lys Leu Gln
1 5

<210> SEQ ID NO 2
<211> LENGTH: 7
<212> TYPE: PRT
<213> ORGANISM: Artificial Sequence
<220> FEATURE:
<223> OTHER INFORMATION: Protein sequence is a substrate for hydrolysis by Fibroblast Activation Protein (FAP)

<400> SEQUENCE: 2

Asp Arg Gly Glu Thr Gly Pro
1 5

<210> SEQ ID NO 3
<211> LENGTH: 38
<212> TYPE: PRT
<213> ORGANISM: Artificial Sequence
<220> FEATURE:
<223> OTHER INFORMATION: Protein sequence is used for targeted delivery into acidic cancer microenvironment -continued

```
<400> SEQUENCE: 3

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35
```

EMETINE DERIVATIVES, PRODRUGS CONTAINING SAME, AND METHODS OF TREATING CONDITIONS USING SAME

CROSS REFERENCE TO RELATED APPLICATIONS

This application is a continuation of U.S. patent application Ser. No. 15/352,290, filed Nov. 15, 2016, which is a continuation of U.S. patent application Ser. No. 13/828,877, filed Mar. 14, 2013, which is a continuation of PCT/US2012/038655, filed May 18, 2012, which claims the benefit of U.S. Provisional Application No. 61/488,601, filed May 20, 2011, which are incorporated herein by reference in their entireties.

FIELD

The disclosure relates to compounds and prodrugs useful for treating a condition or disease, in particular a condition or disease that induces a local decrease in pH or local over expression of an enzyme.

BACKGROUND

It was estimated by the National Cancer Institute (NCI) that 1,529,560 new cases of cancer of all types would occur in 2010 and 569,490 deaths were statistically projected for the same year in the United States. Most solid tumors are uniformly fatal once they have disseminated beyond their tissue of origin. The efficacy of current cancer chemotherapy is limited by systemic toxicity and lack of tumor selectivity, resulting in a variety of side effects. Thus, there is a need to develop cancer-specific agents for the treatment of both metastatic and non-metastatic cancers.

Emetine is a natural product alkaloid found in the root of *Psychotria ipecacuanha*. Emetine has been shown to possess anti-cancer activities via what are believed to be a variety of mechanisms of action. Emetine is an inhibitor of mitochondrial and ribosomal protein synthesis and also interferes with the synthesis and activities of DNA and RNA. Emetine has a very significant anti-cancer potency and its chemotherapeutic action was evaluated up to Phase II clinical trials on several solid tumors about four decades ago. However, it was found that emetine has a very narrow therapeutic index and can cause side effects like muscle fatigue and cardiac toxicity.

It has been reported that N-(2-hydroxypropyl)-methacrylamide (HPMA) copolymer conjugates containing emetine were 60 times less toxic than free emetine in B16F10 melanoma cells and 225 times less toxic in L1210 leukemia cells. It was also reported that the prodrug positively affected the survival of animals with L1210 tumors. However, the prodrug polymer was found to only contain about 8% (wt/wt) of bound emetine and did not significantly affect the rate of tumor growth. These findings discouraged further development of emetine into a clinically useful anticancer drug.

SUMMARY

Compounds are provided herein which are emetine derivatives that can be used as emetine prodrugs which selectively undergo activation to release emetine in specific cellular conditions. In one aspect, a blocking group is incorporated onto the emetine molecule by the derivatization of the N2' position with moieties that can be selectively removed by hydrolysis. Protonation and hydrolysis begins a cascade of one or more reactions in which the bond between the blocking group and the nitrogen at the N2'-position is cleaved with hydrogen replacing the blocking group in the cancer/tumor microenvironment. This exposes the cancer cells to emetine which heretofore was too toxic to be useful for cancer treatment. Such emetine derivatives with the blocking group are less cytotoxic than emetine and are substantially inactive in non-cancerous cells. In one aspect, the compounds described herein can be used for the treatment of metastatic and non-metastatic cancers, including, for example, breast cancer, leukemia, lung cancer, and prostate cancer.

While not intending to be limited by theory, it is presently believed that the protein synthesis inhibitory activity of emetine and consequently its anticancer activity are dependent on the availability of the N2'-position as a secondary amine. It was found that compounds carrying a substituent at the N2'-position show reduced toxicities in cells and tissues at low concentrations and thus do not show the same cardiotoxicity as emetine. Further, the removal of the substituent in cells or tissues will release pure emetine as a potent antitumor agent. In one aspect, selective pH-dependent or enzymatic removal of this substituent in the cancer environment avoids general systemic toxicity and cardiotoxicity of these compounds and ensures that the prodrugs and associated toxicity are targeted to cancer cells.

In one aspect, the compounds provided herein selectively undergo activation to release emetine in acidic pH, such as in the slightly acidic environment of cancer cells. In this aspect, the compound provided herein includes an acid labile functional group linked to the N2'-position of emetine, such as by covalent bond. The covalent bond linking the functional group to the N2'-position of emetine is labile in elevated concentrations of hydrogen ions, such that the covalent bond is hydrolyzed at a pH less than about 7.0, in another aspect at a pH of less than about 6.9, and in another aspect at a pH of less than about 6.8.

In another aspect, compounds which selectively undergo activation to release emetine by enzymatic hydrolysis are provided. Such compounds are useful as prodrugs. In this aspect, enzyme-activated compounds which have emetine coupled to a peptide or other pharmacophore via a self-cleaving linker are provided. The compound is then activated by enzymes preferentially expressed by and/or specific to the cancer cell or immediate environment of the cancer cell.

DETAILED DESCRIPTION

Figure 1:
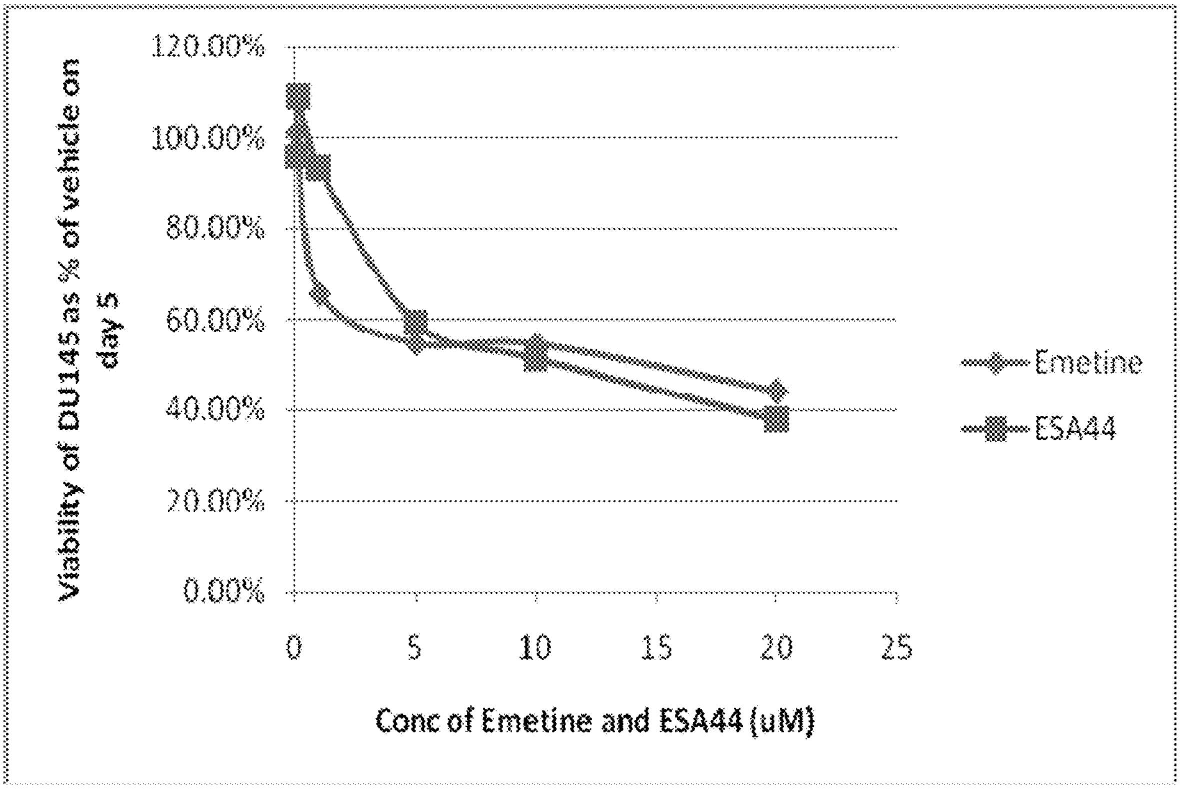
FIG. 1 includes a graph showing the viability of DU145 cells as percent of vehicle on day 5 versus concentration of emetine and Compound 2.

The compounds provided herein include prodrug forms of therapeutic agents with a hydrolyzable group on the N2'-position of emetine. The compounds carry a substituent at the N2'-position. The compounds provided herein selectively undergo activation to release emetine in specific cellular environments by selective pH-dependent or enzymatic removal of the substituent in a desired environment. Emetine has the following structure:

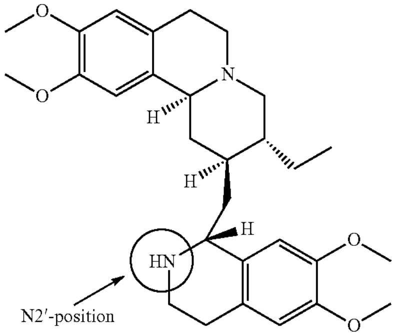

The compounds described herein are useful as prodrugs for the treatment of a variety of medical conditions, including, for example, metastatic and non-metastatic cancers. In one aspect, the compounds are useful as prodrugs for the treatment of breast cancer, leukemia, lung cancer, and prostate cancer.

The compounds described herein can be administered to a subject in substantially stable, inactive form and will remain in substantially stable, inactive form until either hydrolyzed in the acidic environment of the cancer cell or when activated by an enzyme specific to the cancer cell or immediate environment of the cancer cell. By either approach, once in or around the cancer cell, the prodrug is activated by hydrolysis, resulting in the release of free emetine, which is effective to kill the cancer cell and/or prevent its proliferation. While the prodrug may also be activated in non-cancerous cells and possibly harm the non-cancerous cells, the amount of activation in non-cancerous cells is low and toxicity to those cells is minimized.

By one approach, the compounds provided herein include an acid labile functional group "M" linked to the N2'-position of emetine as shown below in formula (I).

Formula (I)

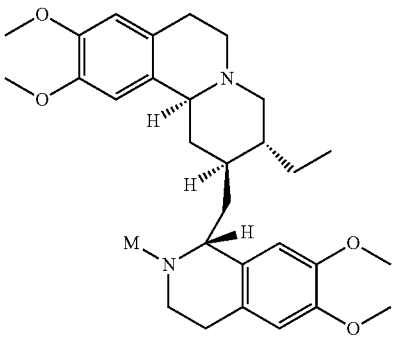

By one approach, the bond between M and the nitrogen at the N2'-position is cleaved at acidic pH, such as in the slightly acidic environment of cancer cells as compared to the higher pH (e.g., about 7.3) of blood and normal cells (e.g., non-cancerous and/or non-infected cells). In one aspect, M is selectively removed at a pH of less than about 7.0, in another aspect less than about pH 6.9, and in another aspect at a pH of less than about 6.8, and the compounds are substantially stable and not hydrolyzed at the higher pH of blood and normal cells. Such selective removal of this group avoids general systemic toxicity and cardiotoxicity of the compounds and ensures that the toxicity of the compounds is substantially targeted to cancer cells. The hydrolysis rate within the cancer cells is high enough to liberate a sufficient quantity of emetine in the cancer cells to be pharmaceutically useful.

In one aspect, Group M is selected from the group consisting of:

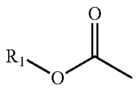, 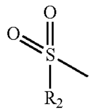, 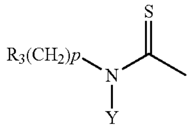,

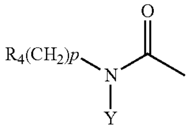, 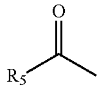, 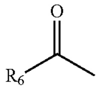, and

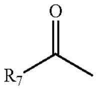, wherein:

R1=

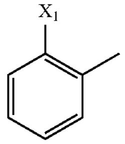 or 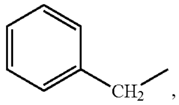,

R2=

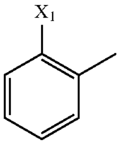

R3=

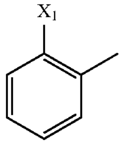 or 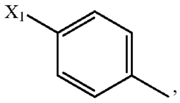,

R4=

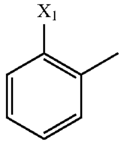 or 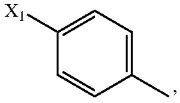,

R5=

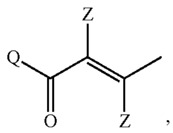

,

R6=

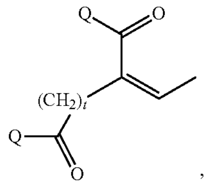

,

R7=

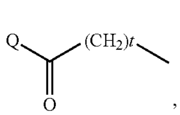

, $X_1$=H, —$NO_2$, —$CO_2X_2$, -$OX_3$, halogen, or C1-C4 alkyl,
$X_2$=C1-C4 alkyl or H,
$X_3$=C1-C4 alkyl or H,
Q=OH, $V^{+-}O^-$,
V=metal ion,
Y=C1-C6 alkyl or H,
Z=H, C1-C4 alkyl, or halogen,
p=0 to 8, and
t=1 to 4.

Other configurations and substituents of Group M may also be provided so long as the group is electron-donating such that the bond between Group M and the N2'-position of emetine is hydrolyzed at a pH of less than about 7.0, in another aspect at a pH of less than about 6.9, and in another at a pH of less than about 6.8, to release emetine in pharmaceutically useful amounts.

In another aspect, Group M has the general formula:

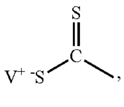

, where V is a metal ion.

In yet another aspect, Group M has the general formula:

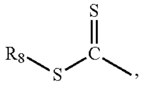

, where $R_8$ is selected from the group consisting of:

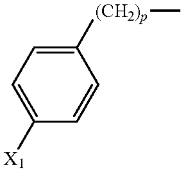

,

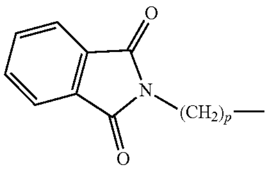

,

-continued

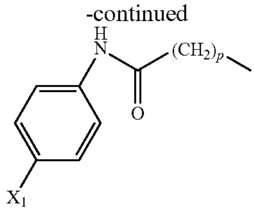

,

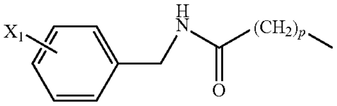

,

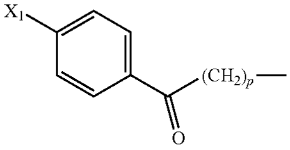

,

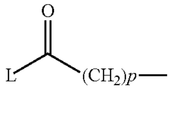

,

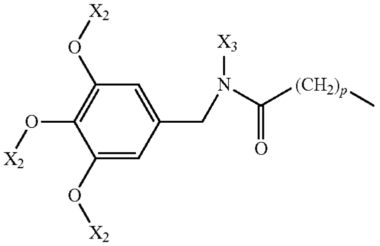

, wherein:
L=$H_2N$— or $H_3CO$—
m=1-3.
n=0-1,
p=0 to 8,
$X_1$=H, —$NO_2$, —$CO_2X_2$, -$OX_3$, halogen, or C1-C4 alkyl,
$X_2$=C1-C4 alkyl or H, and
$X_3$=C1-C4 alkyl or H.

Where V is a metal ion in the compounds described herein, the metal ion may be, for example, sodium or potassium. Other metal ions may also be used, if desired. In one aspect, the metal ion has a valence of 1.

Some of the compounds described herein can comprise one or more asymmetric centers, and thus can exist in various isomeric forms, such as stereoisomers and/or diastereomers. Compounds may be in the form of an individual enantiomer, diastereomer or geometric isomer or may be in the form of a mixture of stereoisomers. In some approaches, the compounds are enantiopure compounds. In other approaches, mixtures of stereoisomers or diastereomers are provided.

Some of the compounds provided herein may have one or more double bonds that can exist as either the Z or E isomer, unless otherwise indicated. In one approach, the compounds are provided as individual isomers substantially free of other isomers and alternatively, as mixtures of various isomers, e.g., racemic mixtures of stereoisomers. In another approach, pharmaceutically acceptable derivatives of these compounds are provided.

It was found that carbamates, thiocarbamates, and dithiocarbamates are often more enzymatically stable than the corresponding amides but are more easily hydrolyzed than amides. The pH of hydrolysis—and thus the ease of hydrolysis—can be tunable depending in the group attached to the N2'-position of emetine. Incorporation of electron-donating groups in $R_1$-$R_8$ above facilitates the acidic cleavage in the lysosome of the cell. For example, acid-catalyzed hydrolysis of a carbamate to carbamic acid followed by spontaneous elimination of carbon dioxide provides emetine in an acidic environment as shown in Scheme 1 below.

SCHEME 1

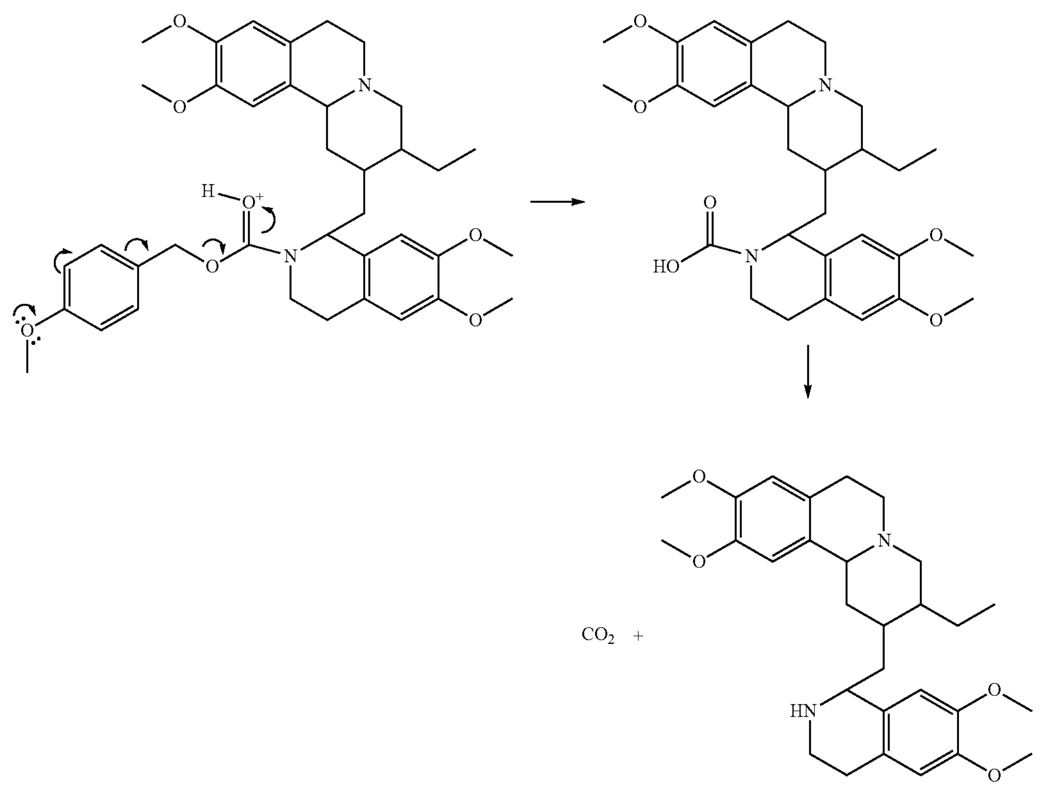

Enzyme Activated Emetine Prodrugs

By another approach, prodrugs provided herein are preferentially activated by one or more enzymes overproduced or selectively produced by cancer cells. The prodrugs are activated by removal of a substituent at the N2'-position of emetine. Removal of the substituent may require one or more hydrolysis and/or self-cleavage steps to provide free emetine. In some approaches, the prodrugs include a peptide sequence of a substituent at the N2'-position of emetine that is hydrolyzed by an enzyme that is predominantly present in cancer cells. Hydrolysis provides an intermediate compound that self-cleaves to provide free emetine.

By one approach, a compound is provided having formula (I):

Formula (I)

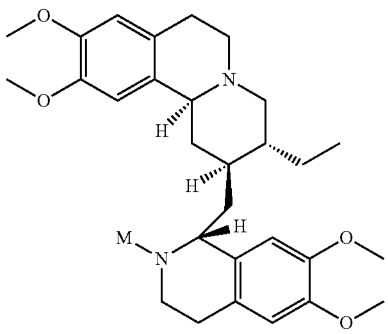

where M is not hydrogen and comprises a substituent effective to be hydrolyzed by an enzyme preferentially expressed by cancer cells. In some aspects, M comprises one of

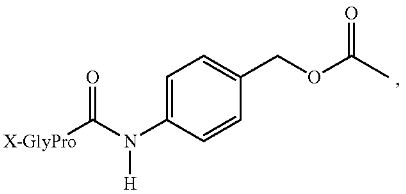
,

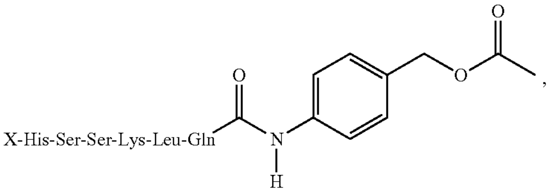
,

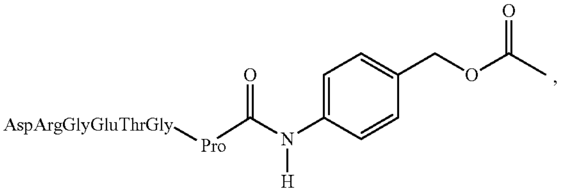
,

-continued

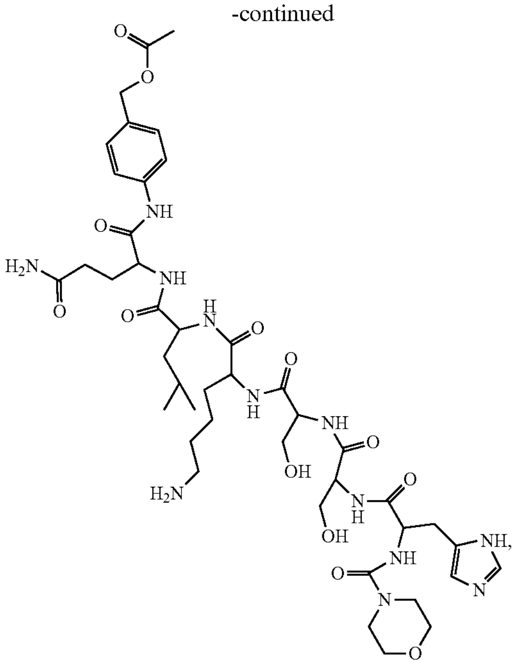

and

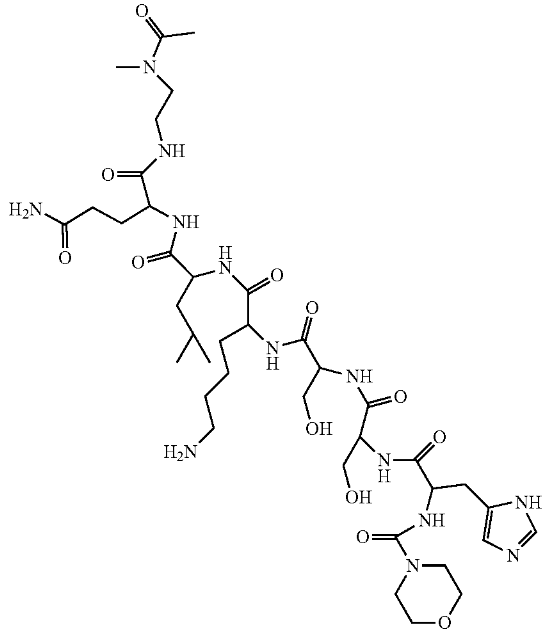

where X is a protecting group or one or more amino acids. For example, the protecting group could include 9-fluorenylmethyloxycarbonyl ("Fmoc"), tert-butyloxycarbonyl ("t-Boc"), acetyl, and morpholino groups. Other protecting groups as are known in the art may also be used, if desired.

In one aspect, the tumor stromal protease fibroblast-activation protein (FAP), a serine protease previously demonstrated to be expressed by stroma of more than 90% of tested human cancers, can be utilized for selective activation of a prodrug in accordance with the present disclosure. FAP is also expressed by mouse stroma within human xenografts. The compounds provided herein include prodrugs containing varying peptide sequences that are hydrolyzable by FAP. The peptide sequences are provided in a group at the N2'-position of emetine. FAP hydrolysis leads to a self-cleaving para-aminobenzylcarbamate intermediate which, upon electronic rearrangement of the linker (self-cleavage), releases free emetine. The release of emetine by this approach is demonstrated in Scheme 2 below.

SCHEME 2

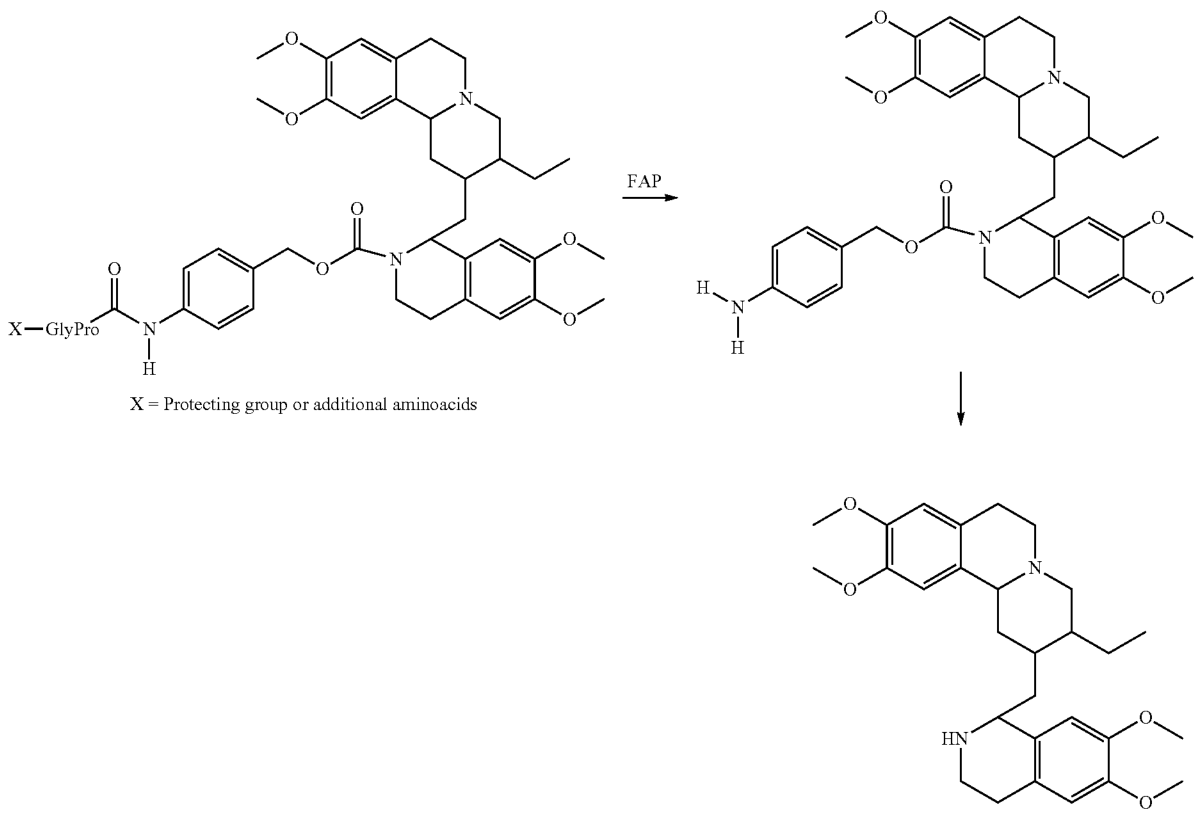

Emetine

In another aspect, a prodrug is provided having a peptide with the amino acid sequence His-Ser-Ser-Lys-Leu-Gln (HSSKLQ) (SEQ ID NO.: 1), that is selectively and efficiently hydrolyzed by Prostate Specific Antigen (PSA). PSA levels in men with prostate cancer can exceed 1000 ng/mL. PSA is enzymatically made inactive by binding to the major protease inhibitors al-antichymotrypsin and α2-macroglobulin, which are generally found at a 104- to 105-fold molar excess in blood serum. However, PSA is found in its active form in the immediate extra-tumoral environment. Thus, PSA can be employed for selective prodrug activation in the immediate extra-tumoral environment. Therefore, emetine prodrugs cleavable by PSA using a peptide comprising the sequence HSSKLQ (SEQ ID NO.: 1) can be used as prostate cancer chemotherapy. A PSA-activated emetine prodrug is shown in Scheme 3 below.

SCHEME 3

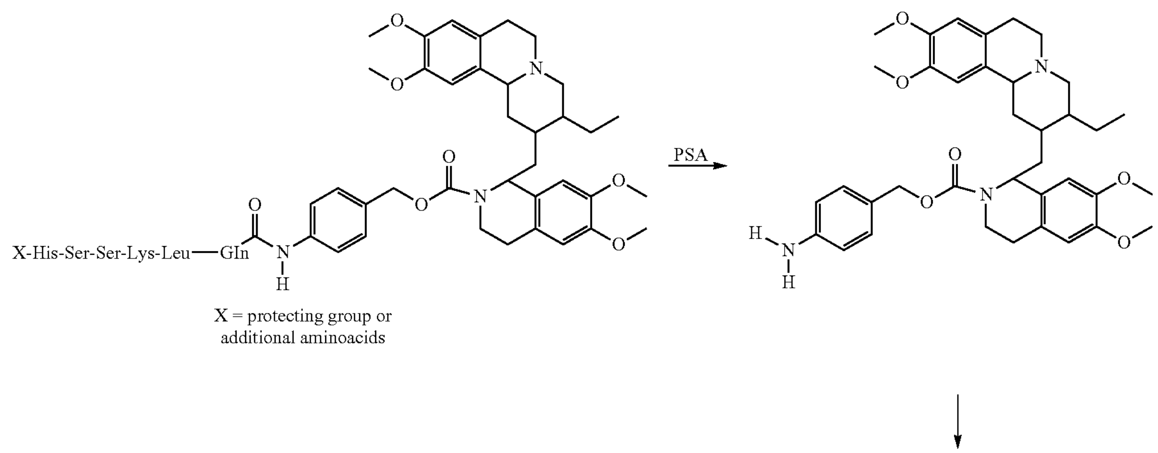

-continued
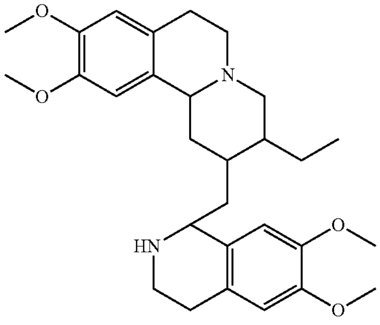
Emetine
In another aspect, a composition comprising a PABA-linked PSA cleavable emetine prodrug is provided. The prodrug is hydrolyzable by Prostate Specific Antigen (PSA) in vivo and in vitro to provide an intermediate that self-cleaves to provide free emetine. A PABA-linked PSA-activated emetine prodrug is shown in Scheme 4 below.
SCHEME 4
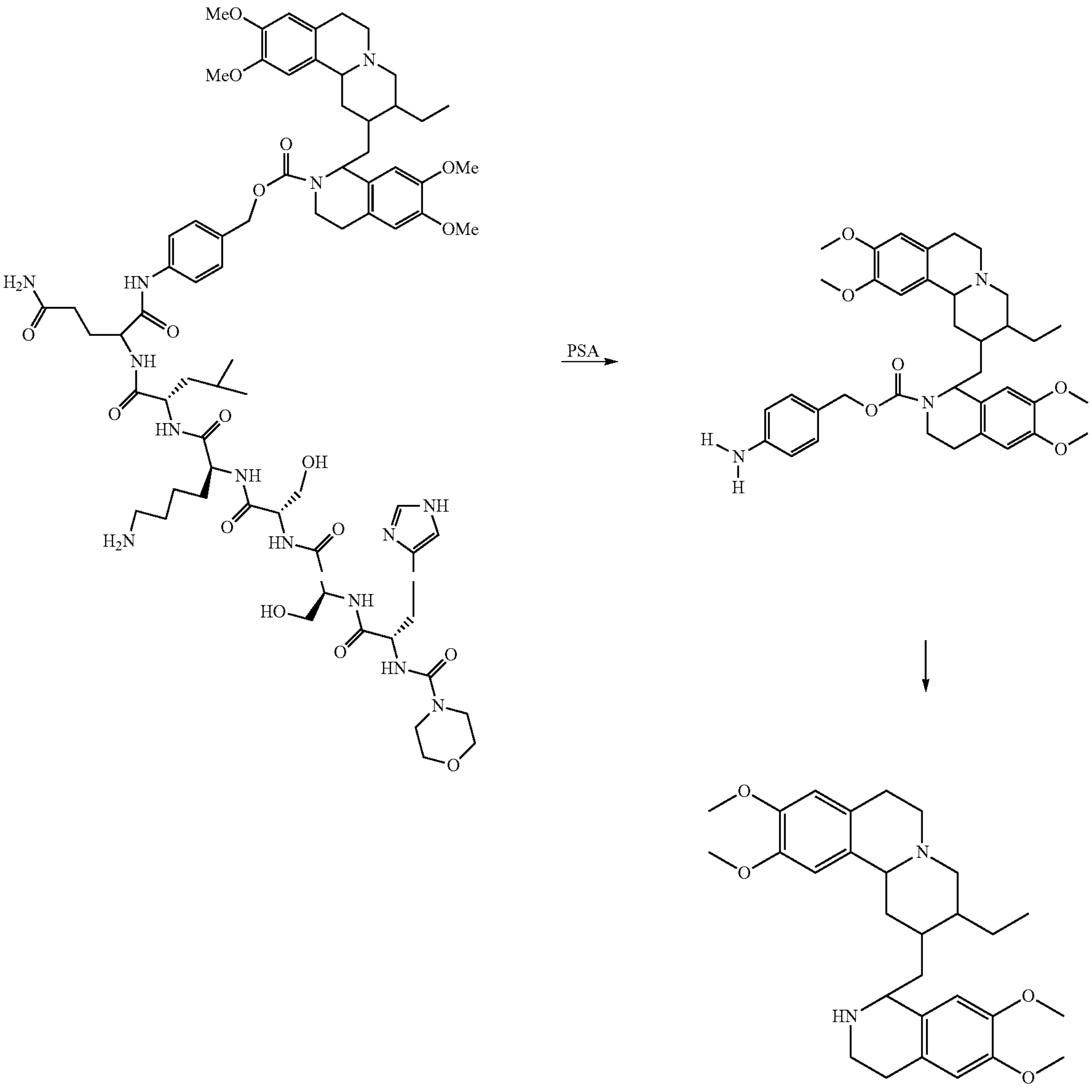
Emetine In another aspect, a composition comprising an ethylene-diamine-linked (EDA-linked) PSA cleavable emetine prodrug is provided. The prodrug is hydrolyzable by PSA in vivo and in vitro to provide an intermediate that self-cleaves to provide free emetine. An EDA-linked PSA-activated emetine prodrug is shown in Scheme 5 below.

SCHEME 5

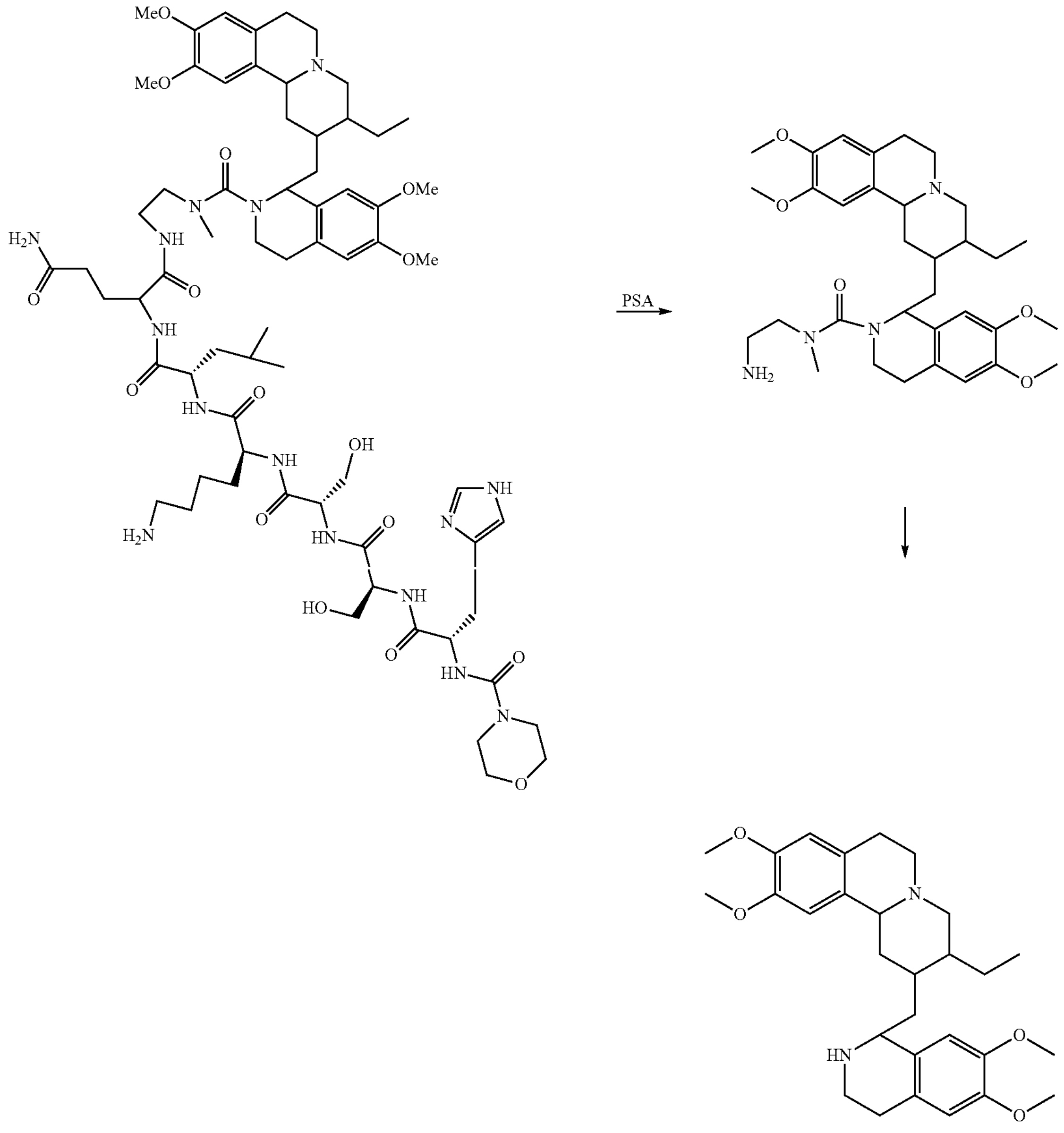

Emetine

In yet another aspect, a PABA-linked emetine prodrug that is cleavable by Fibroblast Activation Protein (FAP) is provided. The prodrug is providing having an amino acid sequence Asp-Arg-Gly-Glu-Thr-Gly-Pro (SEQ ID NO.: 2) that is selectively and efficiently hydrolyzed by FAP in vitro and in vivo. FAP is a 95 kDa glycoprotein expressed by tumor stromal fibroblasts in most cancers. Therefore, FAP can be employed for selective activation of emetine prodrugs cleavable by FAP using a peptide comprising the sequence Asp-Arg-Gly-Glu-Thr-Gly-Pro (SEQ ID NO.: 2), and can be used for cancer treatment.

A PABA-linked FAP-activated emetine prodrug is shown in Scheme 6 below.

SCHEME 6
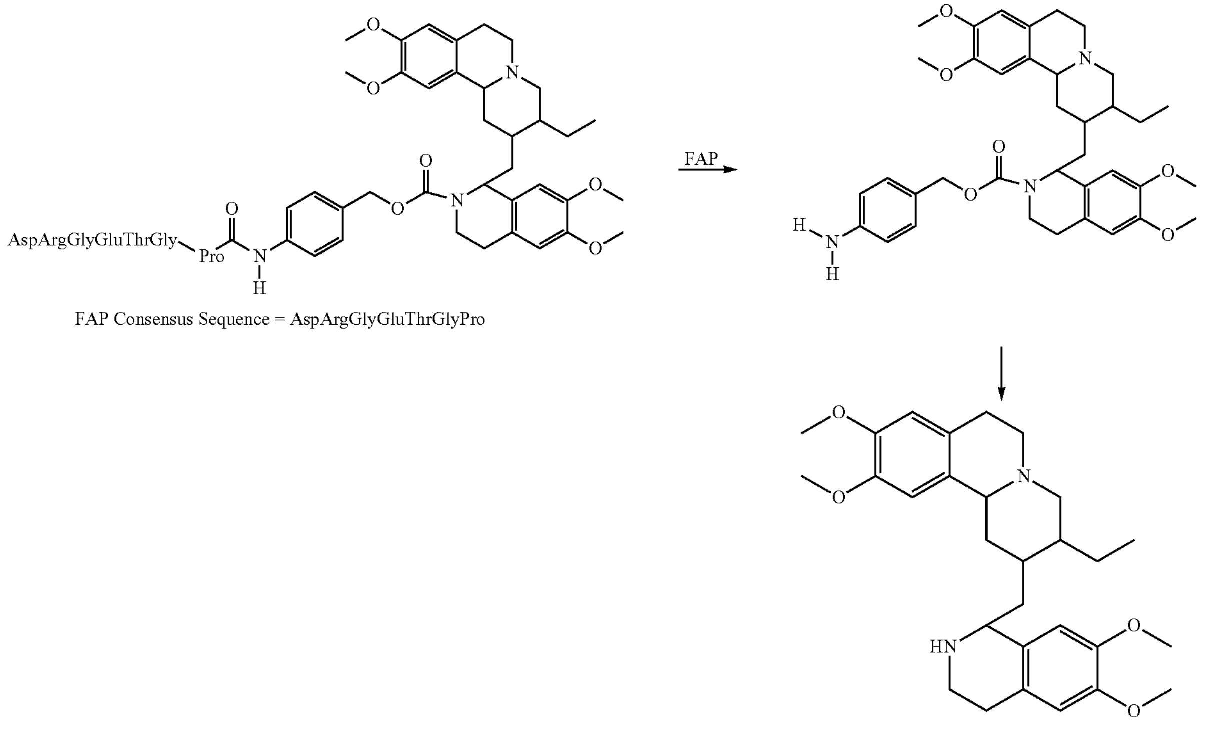
FAP Consensus Sequence = AspArgGlyGluThrGlyPro
Emetine
In yet another aspect, an EDA-linked emetine prodrug that is activatable by FAP as generally described above is also provided. An EDA-linked FAP-activated emetine prodrug is shown in Scheme 7 below.
SCHEME 7
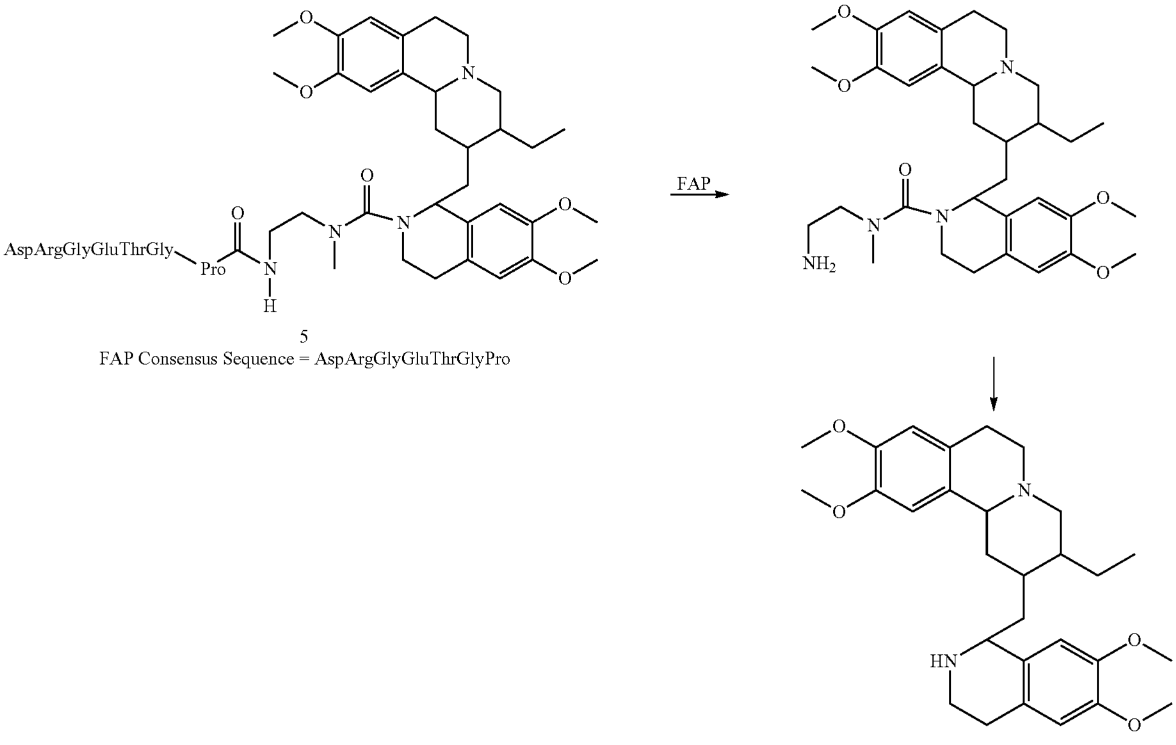
5
FAP Consensus Sequence = AspArgGlyGluThrGlyPro
Emetine In yet another aspect, a pH low insertion peptide (pHLIP)—emetine conjugate is provided. In this aspect, a water-soluble membrane peptide that interacts weakly with the cell membrane at neutral pH is linked at its c-terminus to emetine at the N2'-position. At slightly acidic pH (i.e., less than about pH 7.0), pHLIP inserts into the cell membrane and releases emetine into the cytoplasm. In this approach, emetine is connected to a linker that is conjugated to the inserting C terminus of pHLIP through a disulfide bond that will be cleaved inside the cells, thereby releasing emetine. pHLIP has the following amino acid sequence: AAEQNPIYWARYADWLFTTPLLLLDLALLVDADEGTCG (SEQ ID NO.: 3). A pHLIP-emetine conjugate is provided below. The conjugate is suitable for the targeted delivery of emetine into the acidic cancer microenvironment.

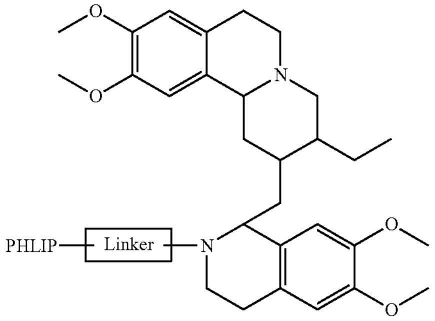

In one aspect, a pharmaceutical composition is provided which comprises a prodrug described herein. The pharmaceutical composition may further comprise a pharmaceutically acceptable adjuvant or vehicle, if desired. Pharmaceutically acceptable adjuvants or vehicles include, for example, Exemplary pharmaceutically-acceptable carriers include saline, buffered saline, isotonic saline, Ringer's solution, dextrose, sterile water, deionized water, glycerol, ethanol, 5% dextrose in water, propylene glycol and combinations thereof.

The compositions described herein may be administered to a subject by a variety of modes of administration. As such, the formulation as well as the concentration of the composition may vary. In one aspect, the compositions may be applied directly to target tissues or organs, or to surrounding fluid or tissue. By one approach, the composition may be administered to a subject via a variety of routes, including, for example, parenterally, particularly intravenously. In one aspect, administration to the desired location may be done by catheter, infusion pump, or stent. Liquid formulations can be prepared, such as, for example, in the form of a solution or suspension in a non-toxic, parenterally-acceptable solvent or diluent. In another aspect, the formulation may be a powder or lyophilate that is reconstituted with a solvent prior to use. In yet another aspect, the formulation may be in the form of an emulsion or liquid concentrate for dilution prior to administration. Exemplary pharmaceutically-acceptable carriers include saline, buffered saline, isotonic saline, Ringer's solution, dextrose, sterile water, deionized water, glycerol, ethanol, 5% dextrose in water, and combinations thereof.

A method for the therapeutic treatment of a medical condition is also provided. The method includes administering to a subject a therapeutically effective amount of a prodrug composition provided herein. Human patients are typically the recipients of the compositions provided herein, although veterinary usage is also contemplated. By one approach, the medical condition being treated is metastatic or non-metastatic cancer, including, for example, breast cancer, leukemia, lung cancer, and prostate cancer. In a more particular aspect, the medical condition is prostate cancer.

In another aspect, a method of delivering emetine to a subject comprising administering to the subject an effective amount of a prodrug compound according to any of the aspects described herein.

In yet another aspect, a method for decreasing the toxicity of emetine is provided, the method comprising synthesizing a prodrug comprising a compound according to any of the aspects described herein.

The following examples are provided to illustrate certain aspects of the disclosure but should not be construed as limiting the scope of the disclosure. Unless specified otherwise, all percentages are by weight.

EXAMPLES

General Methods

Example 1: Synthesis of Dithiocarbamate Ester Derivatives of Emetine

A solution of NaOH or KOH (3 molar equiv.) in water (1.00 ml or about 5% or less of volume of ethanol) and ethanol (20.00 mL) was added to a solution of emetine dihydrochloride hydrate (1.11 g, 2.00 mmol) in ethanol (10.0 ml) at −8° C. This was stirred at this temperature for 15 minutes after which $CS_2$ (0.30 mL, 4.97 mmol, 2.5 molar equiv.) was added. The resulting mixture was stirred at −5 to 1° C. for 2 hours and at room temperature for 30 minutes. The solvent was removed in vacuo and the residue triturated with acetonitrile and then filtered. The filtrate was evaporated to dryness and the residue dissolved in ethyl acetate (3 mL). To this was added diethyl ether which afforded the precipitation of "Compound 1" or "Compound 2," as shown in Scheme 8 below, as a white solid (82.0% yield).

SCHEME 8

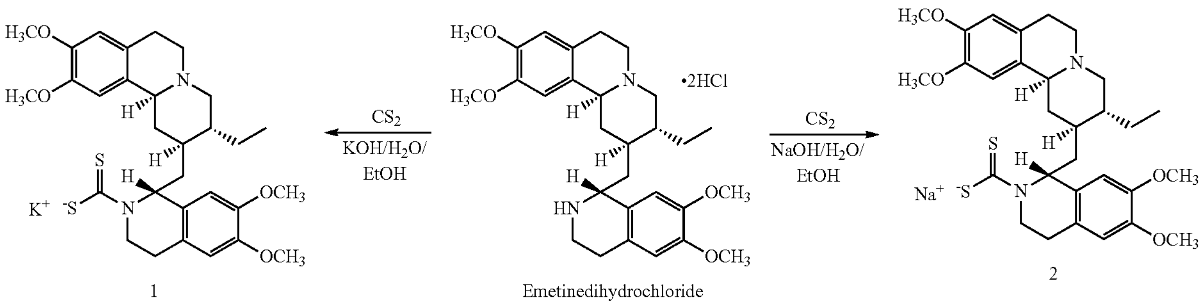

1 Emetinedihydrochloride 2

The dithiocarbamate ester analogs can then be synthesized from the salts of compounds 1 or 2 above as depicted in Scheme 9 below. A Radley's Carousel reaction station with twelve reaction tubes (24 mm×150 mm) was used. Compound 2 (200 mg, 0.35 mmol) was weighed into each of the twelve reaction tubes, and acetonitrile (15 mL) was added to each tube to dissolve the salt. Each of the twelve alkylating agents (0.27 mmol), labeled 3a-31 below, was dissolved in acetonitrile (5 mL). Each reaction tube containing the dissolved salt was then charged with one of the twelve alkylating agents. The reaction tubes were capped and stirred for 24 hours. The mixture in each reaction tube was then transferred to a 100-mL round bottom flask and the solvent was evaporated in vacuo. The residue obtained after evaporation of the solvent was triturated with water (20 mL) to dissolve any inorganic substances and then filtered under suction. Each crude product was air-dried and then purified by flash chromatography on silica gel using EtOAc:MeOH (10:1) as eluent.

SCHEME 9

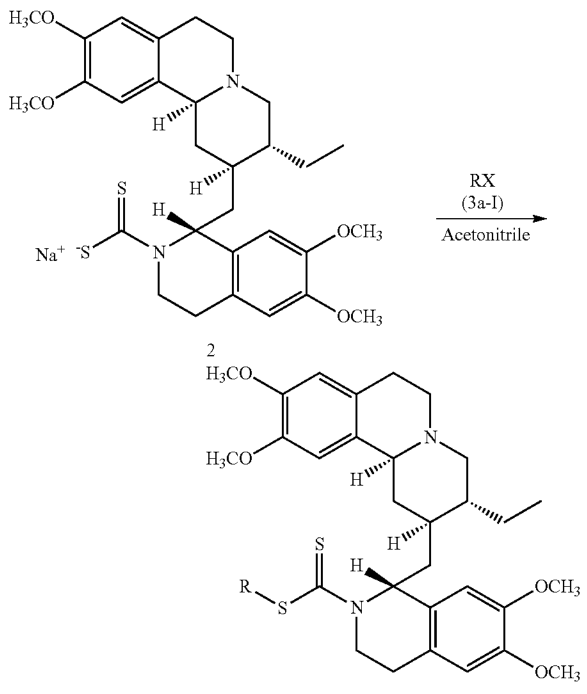

2

(4a-I)

Alkylating agents (RX) useful herein include, for example, the following:

3a

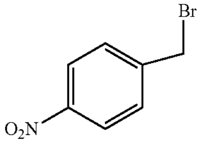

3b

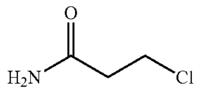

-continued

3c

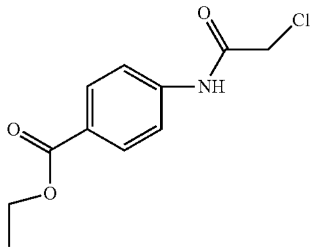

3d

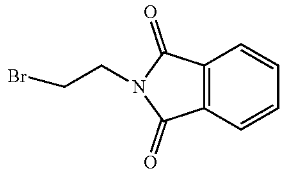

3e

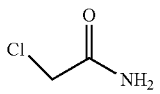

3f

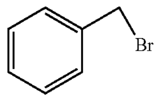

3g

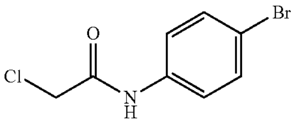

3h

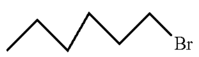

3i

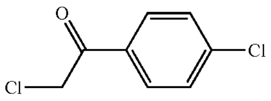

3j

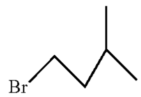

3k

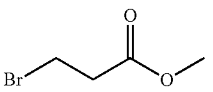

-continued
31
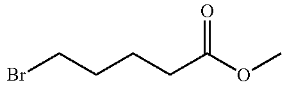
The following dithiocarbamate ester analogs of emetine (4a-4l) were obtained:
4a
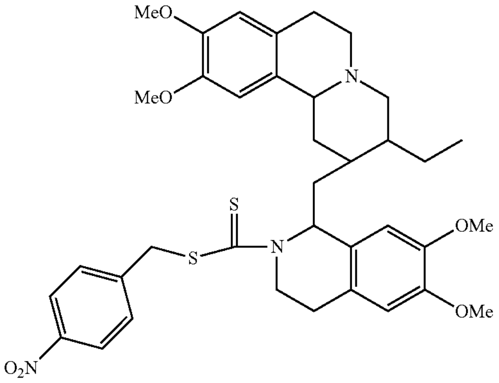
4b
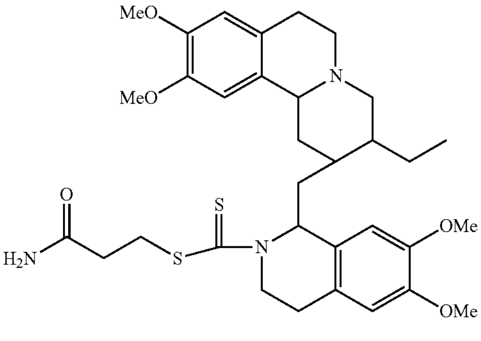
4c
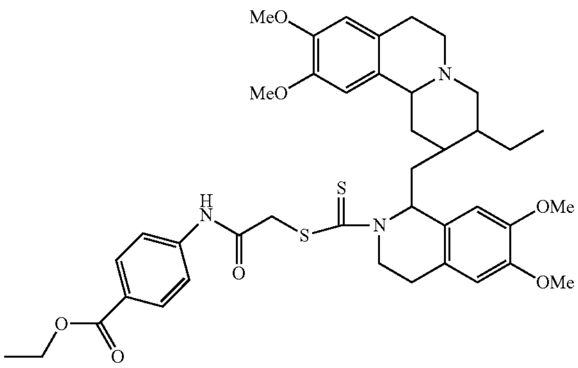
-continued
4d
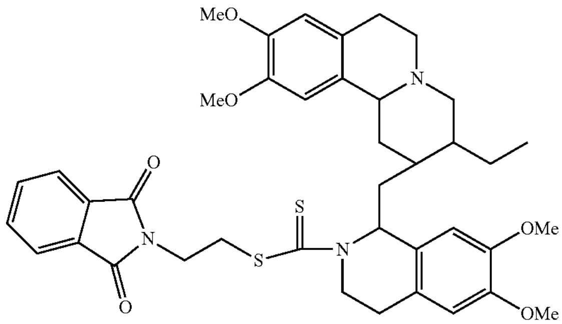
4e
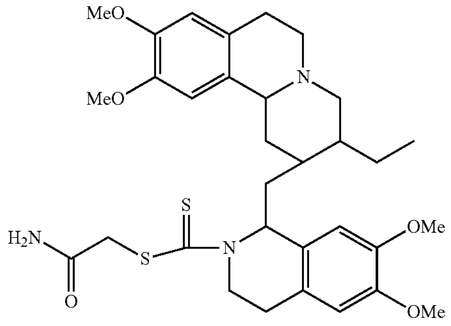
4f
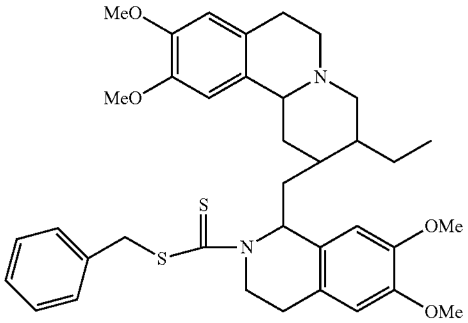
4g
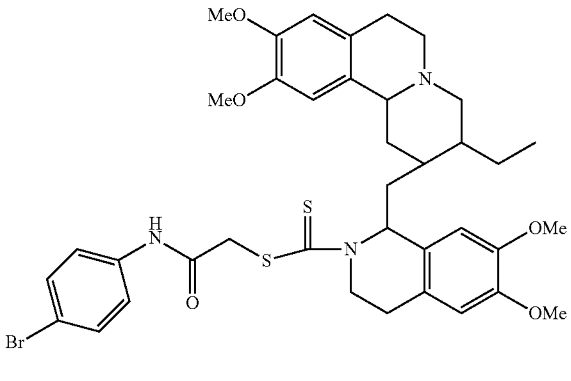

-continued

4h

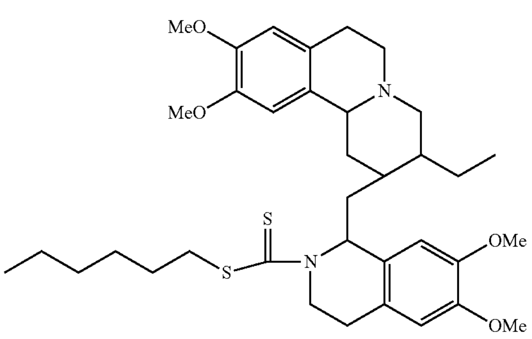

4i

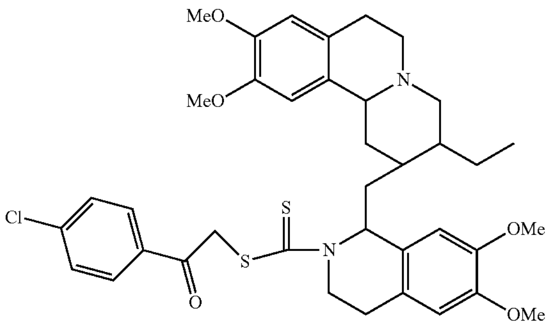

4j

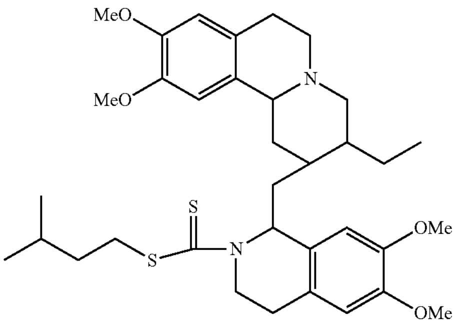

4k

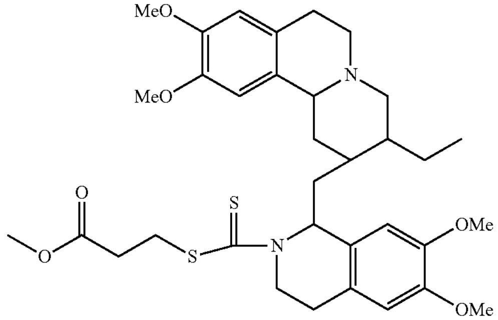

-continued

4l

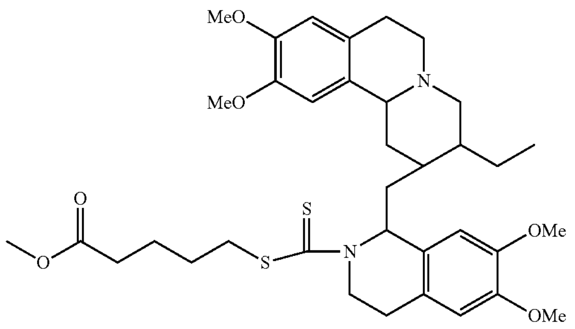

Example 2: Synthesis of Carbamate Derivatives of Emetine

Emetine dihydrochloride (1.0 molar equiv.) was added at room temperature to a stirred solution of dimethyl amino pyridine (DMAP) or triethyl amine (4.0 molar equiv.) in chloroform. After ten minutes, the appropriate chloroformate (4 molar equiv.) was added. The reaction mixture was then stirred at room temperature for 12-24 hours. The solvent was removed in vacuo and the residue was dissolved in $CH_2Cl_2$ (25 mL) and washed with water (2×20 mL) and brine (1×20 mL). It was then dried over anhydrous $MgSO_4$ and solvent was evaporated under reduced pressure. The crude product was purified by column chromatography on silica gel eluting with 100% EtOAc to EtOAc:MeOH 7.5:2.5 to give the desired product. The reaction scheme for synthesis of carbamate ester analogs of emetine is shown in Scheme 10 below.

SCHEME 10

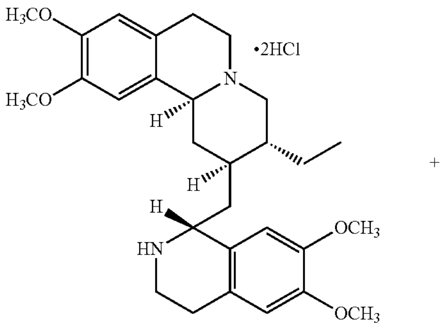

Emetinedihydrochloride

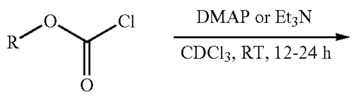

-continued

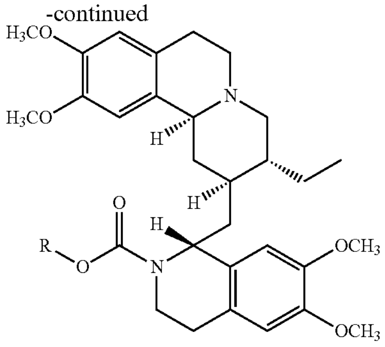

5a-c

The following carbamate ester analogs of emetine (5a-5c) were obtained:

5a

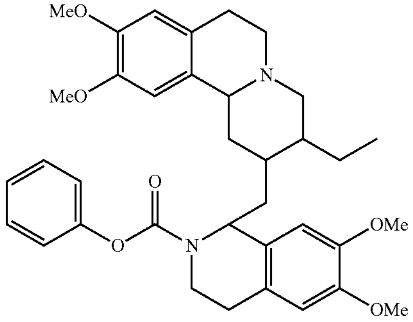

5b

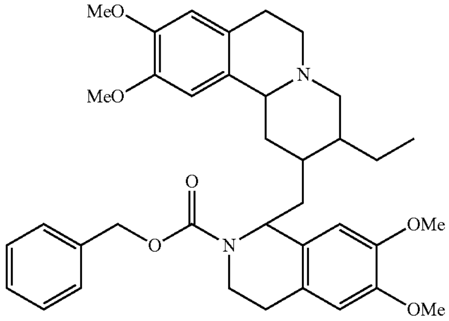

5c

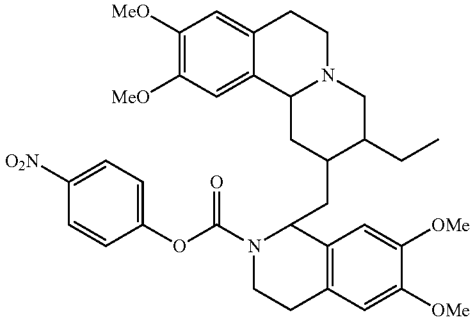

Example 3: Synthesis of Sulfonamide Derivatives of Emetine

To a stirred solution of dimethyl amino pyridine (DMAP) (4 molar equiv). in $CH_2Cl_2$ (20 mL) was added emetine dihydrochloride (1 molar equiv) at room temperature. After 15-20 minutes, the appropriate sulfonyl chloride (2.5 molar equiv) solution in $CH_2Cl_2$ was added. The reaction mixture was then stirred at room temperature for 12-16 h. The solvent was removed in vacuo and water (25 mL) was added to the residue to dissolve all the water soluble impurities. Then the crude product was isolated by extraction into $CH_2Cl_2$ (3×25 mL). The combined organic phase was then washed with brine (2×20 mL), dried over anhydrous $MgSO_4$ and filtered. Solvent was evaporated under reduced pressure. The crude product was purified by column chromatography on silica gel using gradient elution starting with 100% $CH_2Cl_2$ to remove the least retained impurities and gradually varying this to $CH_2Cl_2$:MeOH eluent mixture with optimum MeOH components varying from 5 to 20% depending on the specific analog (8a-80 to afford the desired product. The reaction is illustrated below in Scheme 11.

SCHEME 11

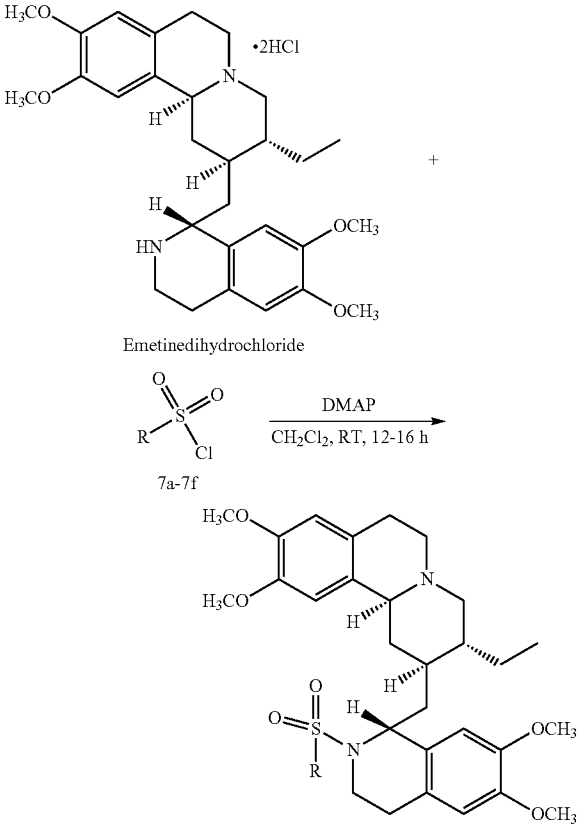

Emetinedihydrochloride 7a-7f 8a-f

The following sulfonamide analogs of emetine (8a-8f) were obtained:

8a

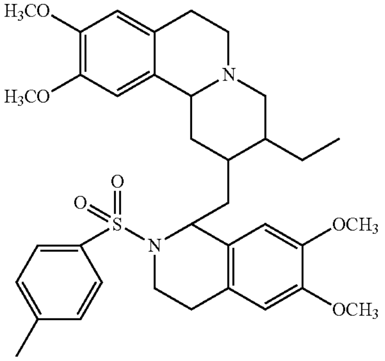

-continued

8b

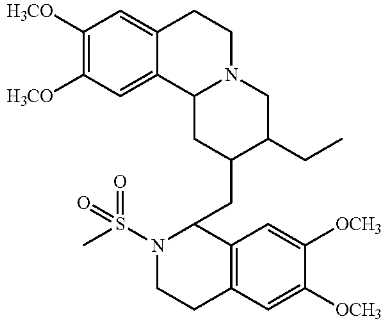

8c

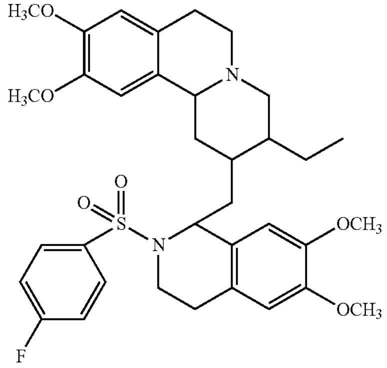

8d

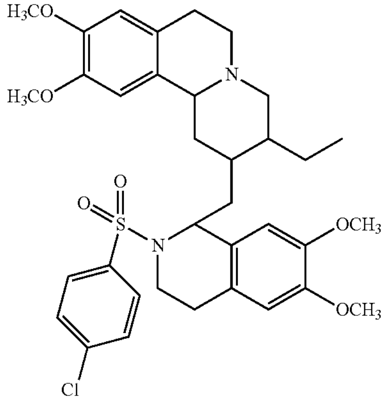

8e

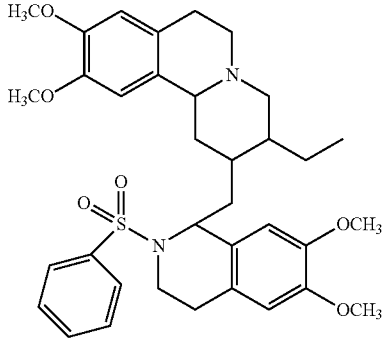

-continued

8f

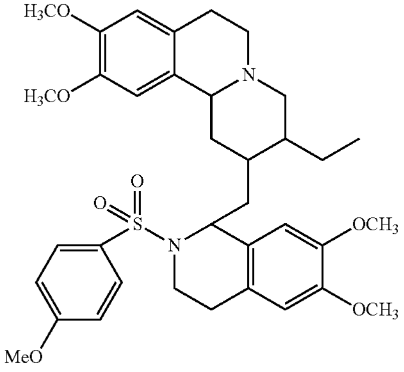

Example 4: Synthesis of Thiourea Derivatives of Emetine

The general reaction scheme for synthesis of thiourea analogs of emetine is shown in Scheme 12 below.

SCHEME 12

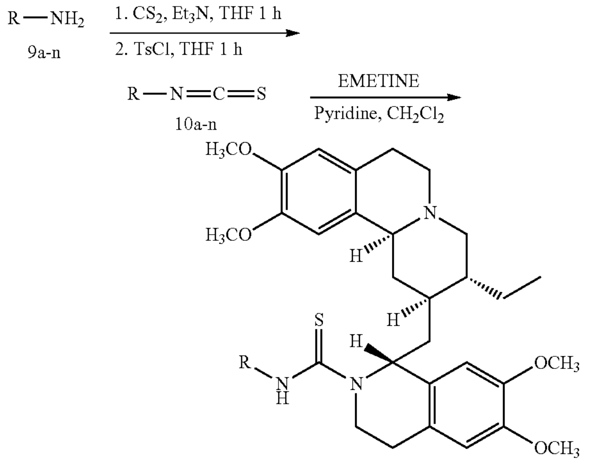

11a-n

Isothiocyanates were first synthesized according to JOC: 72, 3969-3971 (2007), which is incorporated herein by reference, with slight modification. To a solution of appropriate amine (16.0 mmol, 1 molar equiv.) in THF (15 mL) at 0° C. was added triethylamine (10.0 mL). The resultant mixture was kept stirring while $CS_2$ (34.0 mmol, 2 molar equiv.) was added dropwise over about thirty minutes at 0° C. The mixture was allowed to stir at this temperature for fifteen minutes after which it was stirred at room temperature for one hour. The reaction mixture was then cooled to 0° C. again while stirring continued, and a solution of tosyl chloride (20.8 mmol, 1.3 molar equiv) in THF was added gently. The reaction mixture was allowed to warm up to room temperature, stirred for an additional hour at room temperature and then 20 mL 1N HCl was added while stirring continued. This was followed by 25 mL diethyl ether and the reaction was stirred for another five minutes. The aqueous layer was separated and then back extracted with diethyl ether (2×20 mL). The combined organic layers were dried over $Na_2SO_4$, solvent evaporated in vacuo, and the crude product was purified by column chromatography eluting with hexanes over silica gel to give pure isothiocyanate which was used in the next synthesis step.

The second step is synthesis of thiourea analogs of emetine from isothiocyanate. To a stirred solution of pyridine or triethylamine (0.5 mL) in $CH_2Cl_2$ (15 mL) at room temperature was added emetine dihydrochloride (200 mg, 0.36 mmol, 1 molar equiv.). After all the emetine was completely dissolved, the appropriate isothiocyanate, 10a-n, (0.72 mmol, 2 molar equiv.) was added. The reaction mixture was stirred at room temperature for 8 to 16 hours. $CH_2Cl_2$ (15 mL) was then added to the mixture which was subsequently washed with water (2×25 mL) and brine (1×25 mL). The organic layer was dried over $MgSO_4$ and the solvent removed in vacuo. The crude product was purified either by precipitation in a diethyl ether/hexane mixture or by column chromatography using $CH_2Cl_2$/MeOH mixture in appropriate ratio as eluent. Compounds 11a-d and 11f-h were purified by precipitation in a 1:1 and 3:7 mixture (respectively) of diethyl ether and hexanes; whereas 11e, and 11i-n were all purified by column chromatography over silica gel using gradient elution. Elution with 100% $CH_2Cl_2$ separated the nonpolar impurities in all of them while 10% MeOH in $CH_2Cl_2$ was the best eluent to afford pure 11e, 11i and 11j. However, 5% MeOH in $CH_2Cl_2$ was the optimum eluent system for obtaining pure form of 11k-n.

The following thiourea analogs of emetine (11a-11n) were obtained:

11a

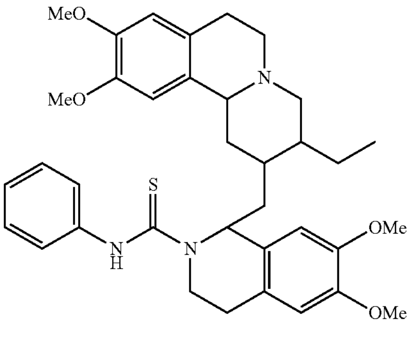

11b

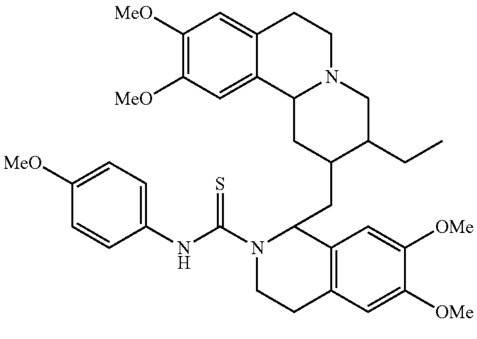

-continued

11c

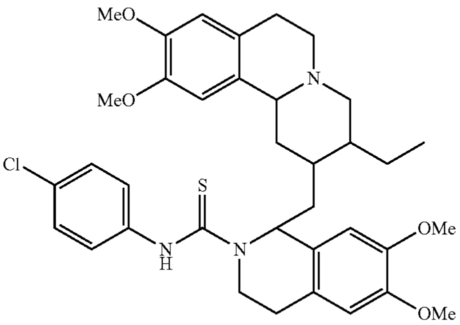

11d

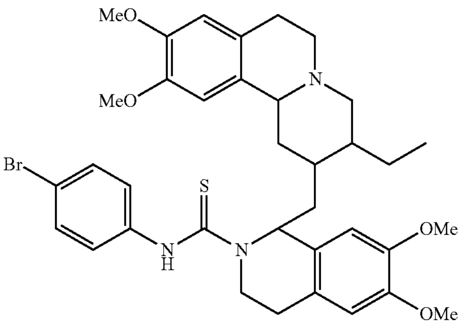

11e

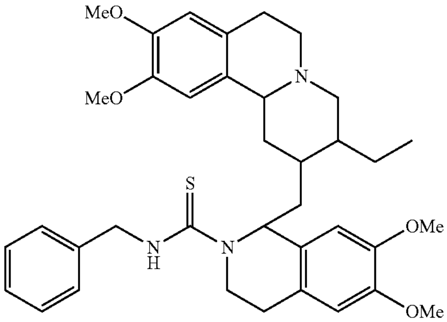

11f

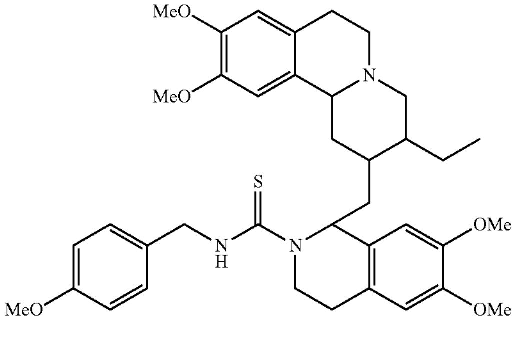

-continued
11g
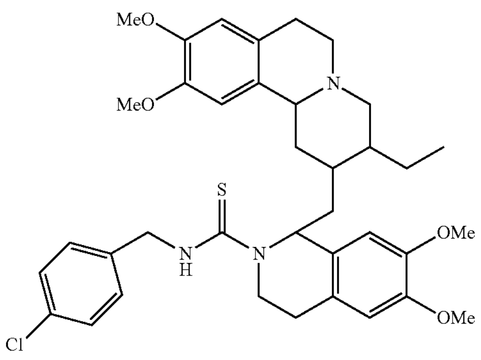
11h
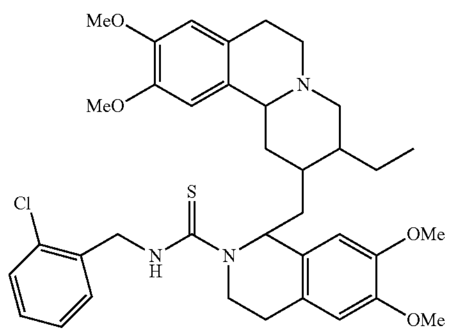
11i
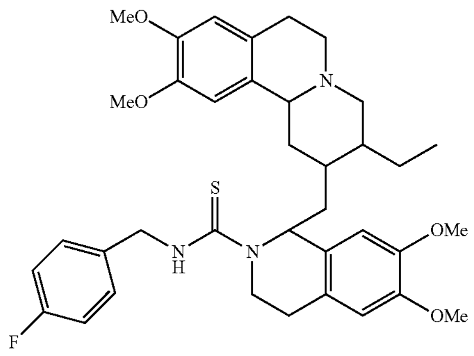
11j
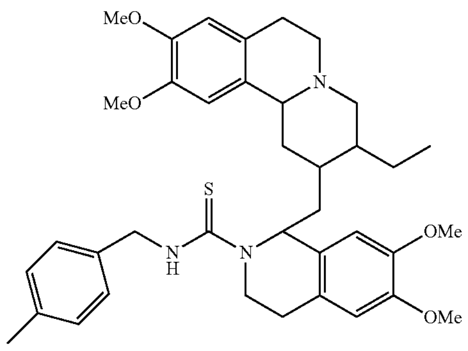
-continued
11k
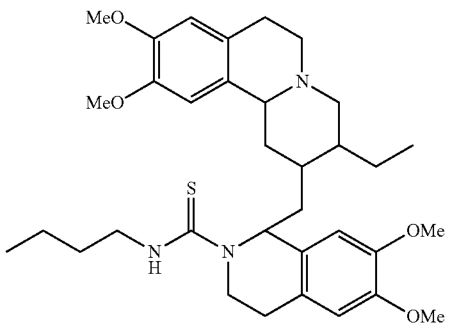
11l
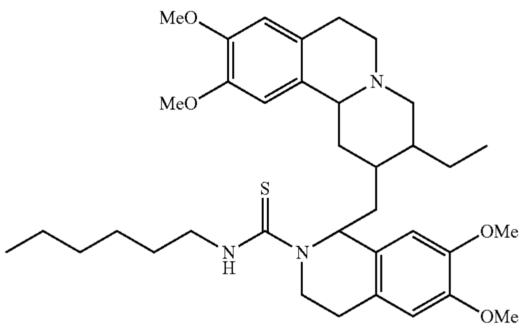
11m
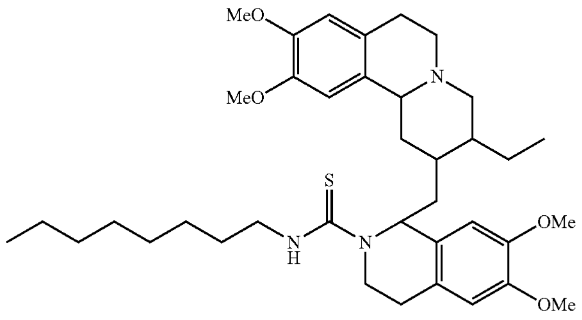
11n
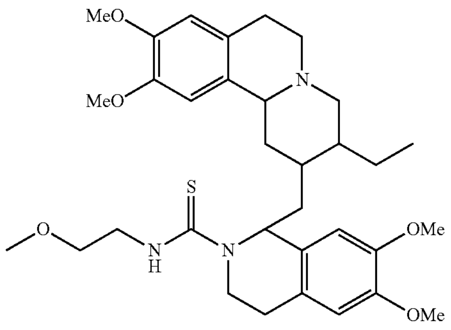
Example 5: Synthesis of Urea Analogs of Emetine
The synthesis of urea analogs was done in two stages as shown in Scheme 13 below.

SCHEME 13

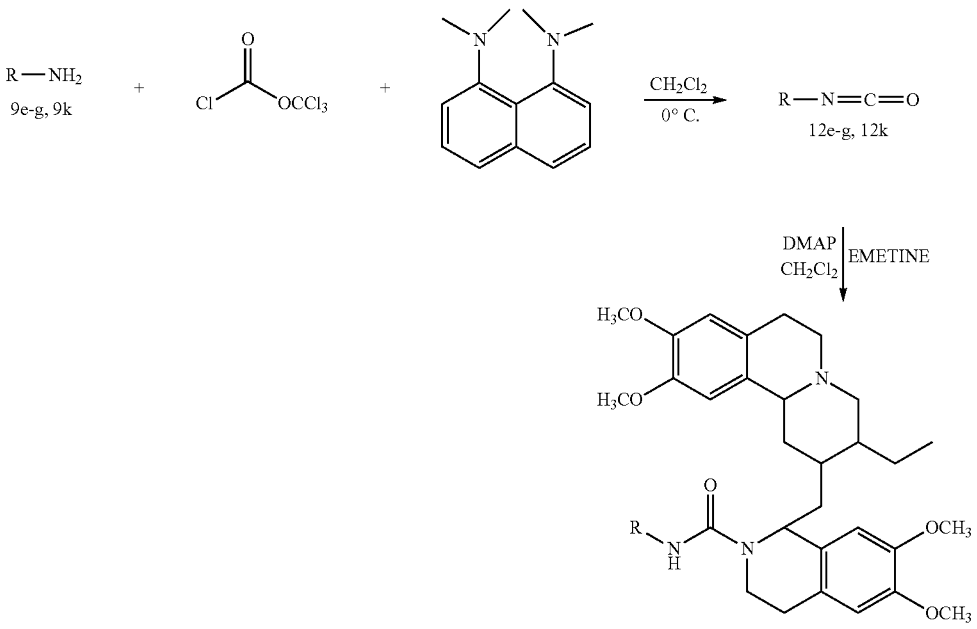

13e-g, 13k

First, isocyanates were synthesized from an appropriate amine, using a two-step but one pot reaction. The procedure was reported in JOC 1996, 61, 3883-3884, which is incorporated herein by reference. The isocyanates were then reacted with emetine to make the urea analogs.

A solution of trichloromethyl chloroformate (5.741 mmol, 1.5 molar equiv) in $CH_2Cl_2$ (15 mL) at 0° C. was set stirring. To this was added dropwisely a solution containing a mixture of an appropriate amine, 9e-g and 9k, (3.827 mmol, 1 molar equiv) and 1,8-bis(dimethylamino)-naphthalene or DMAP (7.654 mmol, 2 molar equiv) over about 5 to 10 min. Thereafter, the ice bath was removed and the reaction mixture was allowed to warm up to room temperature and then stirred for another 45 min. Solvent and all volatiles were evaporated in vacuo and fresh $CH_2Cl_2$ 30 mL was added followed by 1N HCl solution (20 mL); this was stirred for about 3-5 min. The organic layer was separated and then washed with 1 N HCl (3x15 mL) and 1 N NaOH (1x15 mL). It was dried over $Na_2SO_4$ and solvent was evaporated in vacuo to give the respective isocyanates, 12e-g and 12k, that were used without further purification.

To a solution of a given isocyanate, 12e-g and 12k (0.72 mmol, 2 molar equiv.) in $CH_2Cl_2$ (10 mL), was added a solution of emetine dihydrochloride (200 mg, 0.36 mmol, 1 molar equiv) and DMAP (1.44 mmol, 4 molar equiv.) mixture in $CH_2Cl_2$ (15 mL) at room temperature. The reaction mixture was stirred overnight at room temperature. 10 mL $CH_2Cl_2$ was then added to the mixture which was then washed with water (2x25 mL) and brine (1x25 mL). The organic layer was then dried over $MgSO_4$ followed by solvent removal in vacuo. All the products were purified by column chromatography using gradient elution beginning with 100% EtOAc to an eluent containing 10% MeOH in EtOAc to afford pure 13e-g and 13k.

The following urea analogs of emetine (13e-g and 13k) were obtained.

13e

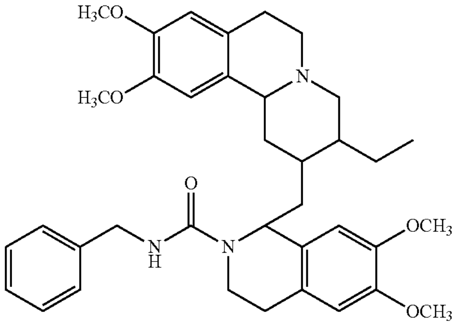

13f

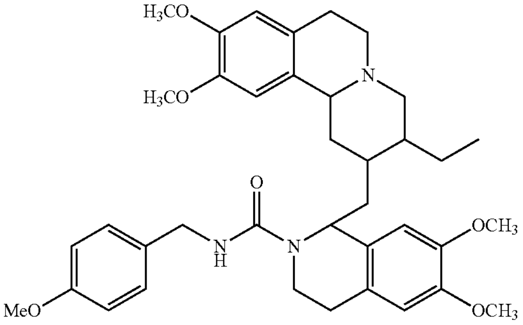

-continued

13g

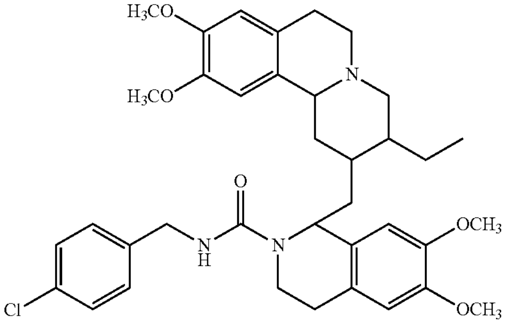

13k

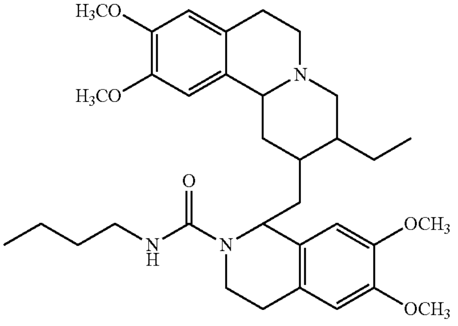

Example 6: Synthesis of Amide Derivatives of Emetine

A solution of emetine dihydrochloride (1 molar equiv) in a chloroform (10 mL to 500 mg emetine) and triethylamine (2 mL) was stirred for about 5 minutes. To this was added a solution of the appropriate anhydride 14a-e (4 molar equiv.) in chloroform. This reaction mixture was stirred for 8 to 20 hours at room temperature. MALDI-MS was utilized to qualitatively determine the formation of the desired product in the reaction mixture. All volatiles and solvent was evaporated in vacuo from the reaction mixture to give the crude products of the amide analogs 15a-e. Purification methods vary slightly from one analog to another and these are specified below. The general reaction scheme is shown below.

SCHEME 14

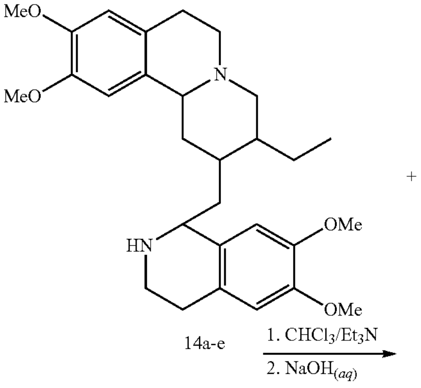

-continued

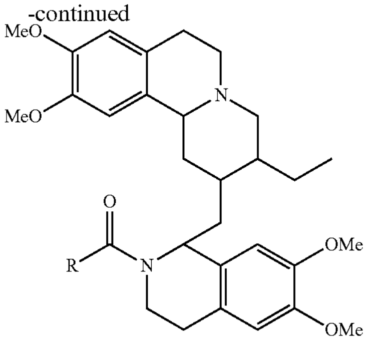

15a-e

The anhydrides 14a-e

14a

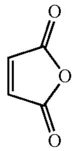

14b

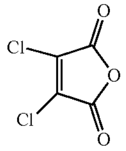

14c

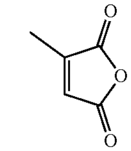

14d

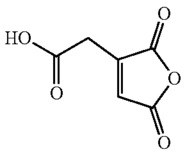

14e

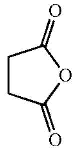

For compounds 15a, b, and e, the crude product was dissolved in about 40 mL of chloroform. This was washed with water (2×20 mL) and the organic phase later washed with an aqueous solution containing 5% 2N NaOH in distilled water (1×20 mL) to remove all the triethyl amine and then obtain sodium salt at the carboxylate end of these amides. The organic phase was later washed with brine (15 mL×2) and then dried with $MgSO_4$. Solvent was completely evaporated in vacuo at a temperature not greater than 45° C. The crude product obtained was dissolved in as little ethyl acetate as possible (about 1.0 mL of ethyl acetate for a reaction of 500 mg of emetine·2HCl). Hexanes (about 15-20 mL) were then added to this mixture in order to precipitate the pure products which were filtered under vacuum and then washed with a lot of hexanes. The solid products obtained (white to pale yellow) were then dried in vacuum over at 70° C. for 4 hours in order to remove all traces of solvent impurities.

For compounds 15c and d, the crude product was dissolved in 50 mL of chloroform, and then washed in water (1×20 mL). This must be done very gently and carefully to avoid emulsion formation. Then it was washed with a solution of 5% 2 N aqueous NaOH in brine (2×20 mL). The organic phase was later washed in 100% brine (1×20 mL), and then dried over $MgSO_4$. Solvent was evaporated in vacuo at a temperature not greater than 45° C. The crude product obtained was dissolved in as little ethyl acetate as possible (about 1.0 mL of ethyl acetate for a reaction of 500 mg of emetine·2HCl). Hexanes (about 15-20 mL) was then added to this mixture in order to precipitate the pure products which were filtered under vacuum and then washed with a lot of hexanes. The solid products obtained (white to pale yellow) were then dried in vacuum over at 70° C. for 4 hours in order to remove all traces of solvent impurities.

The following products were obtained:

15a1

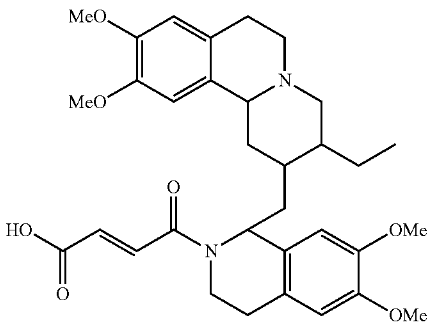

15a2

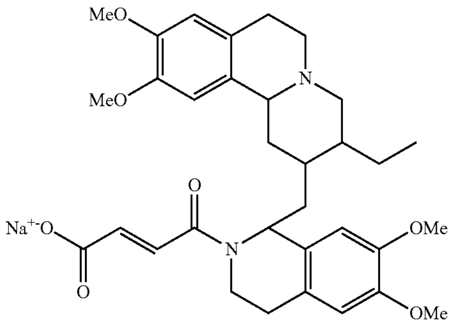

15b1

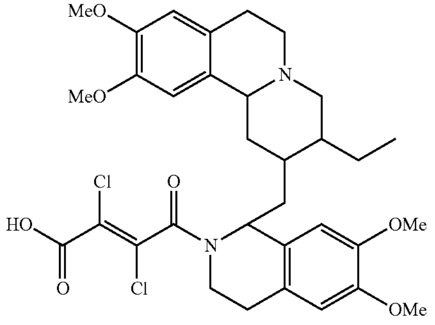

-continued

15b2

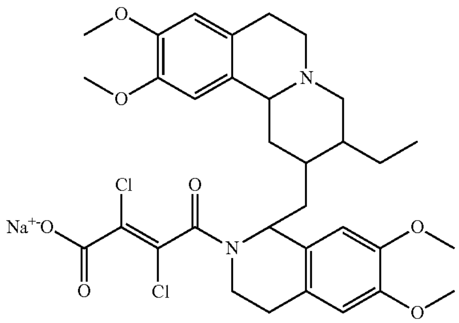

15c1

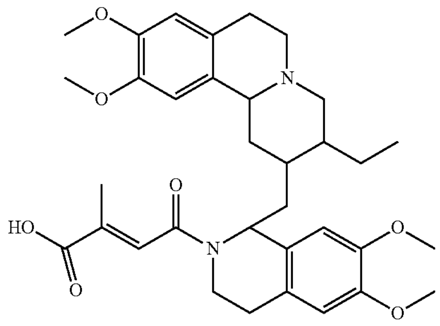

15c2

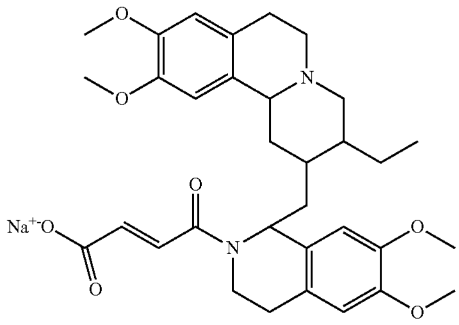

15d1

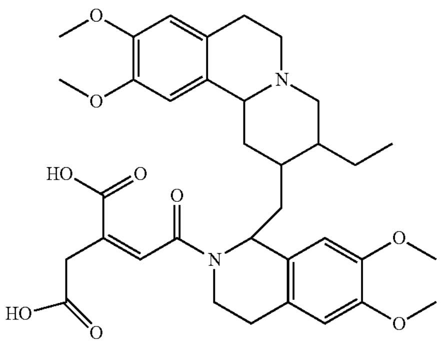

-continued

15d2

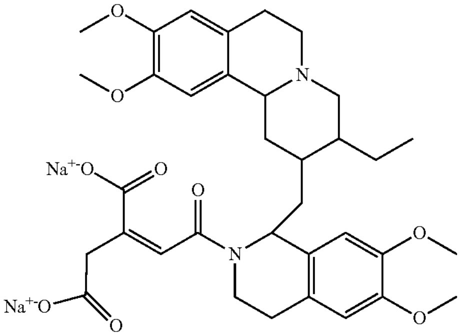

15e1

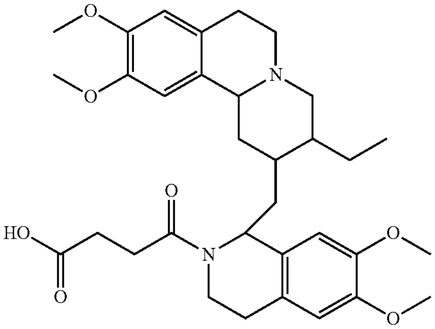

15e2

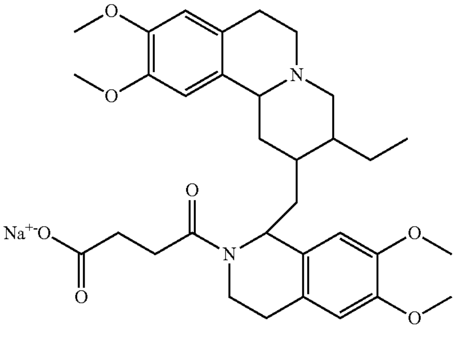

Example 7: Synthesis of Carbamate and Thiocarbamate Derivatives of Emetine

Carbamate and thiocarbamate derivatives can be synthesized from chloroformates or chlorothioformates in high yield by employing the Schotten-Baumann procedure as outlined in Scheme 15 below.

SCHEME 15

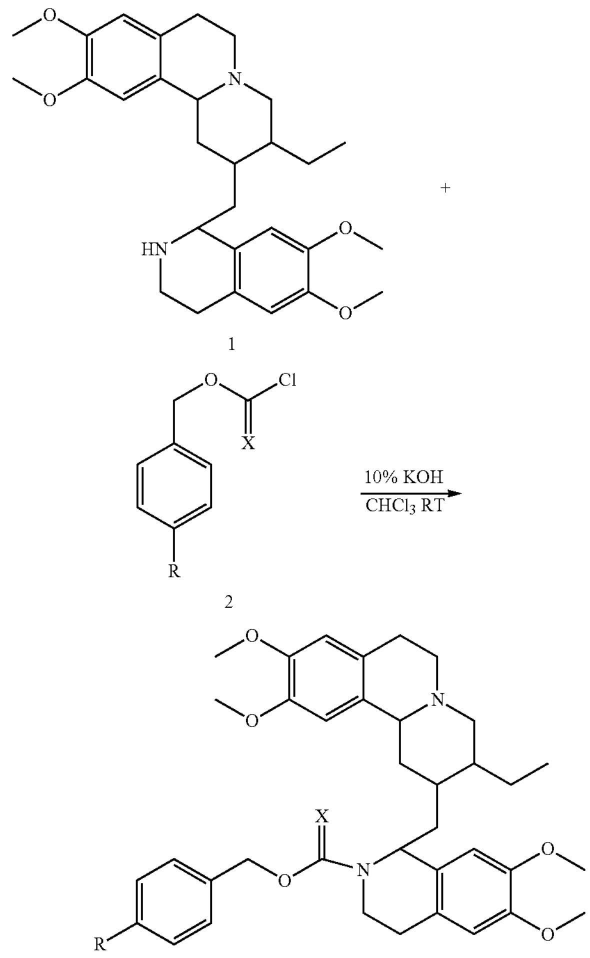

1 + 2 → 3

Example 8: Synthesis of Dithiocarbamate Derivatives of Emetine

The synthesis of dithiocarbamate esters is accomplished by converting emetine to the potassium dithiocarbamate salt followed by straightforward $S_N2$ reaction of the salt with various benzyl halide derivatives as shown in Scheme 16.

SCHEME 16

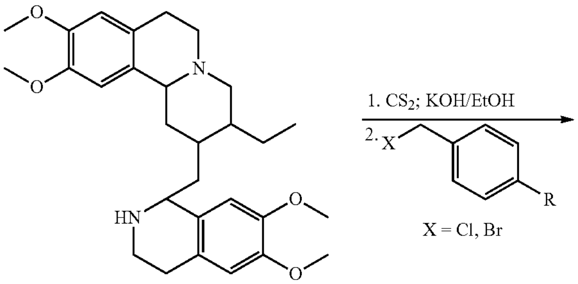

1

-continued

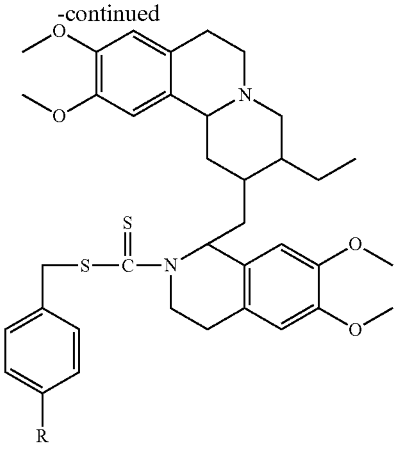

4

Example 9: Cytotoxicity of Emetine and Compound 2

Figure 2:
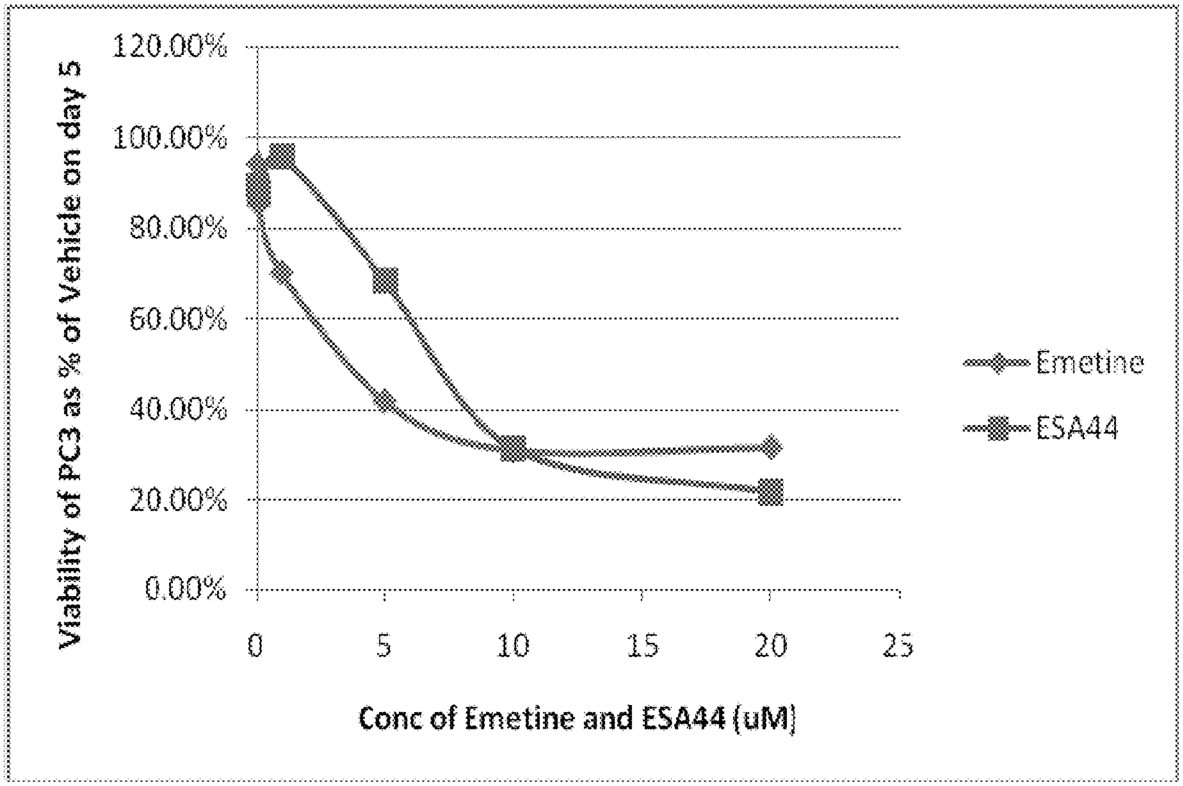
FIG. 2 includes a graph showing the viability of PC3 cells as percent of vehicle on day 5 versus concentration of emetine and Compound 2.

The cytotoxicity of emetine and Compound 2 (as produced above in Example 1 and referred to in the figures as "ESA44") was evaluated in DU145 and PC3 cells using 100% confluent cells. Cells were plated at 40,000 cells per well and allowed to grow for 4 days until the pH of the medium was 6.7. Compound 2 was added in RPMI, pH 7.0. The effect of the pH on the hydrolysis of Compound 2 to release emetine was evaluated. FIGS. 1 and 2 are graphs showing the viability of DU145 and PC3 cells as percent of vehicle on day 5 versus concentration of emetine and Compound 2. The results suggest that Compound 2 is hydrolyzed into emetine under more acidic conditions.

The $IC_{50}$ values (in μM) are presented in Table 1 below.

TABLE 1

| | Emetine | Compound 2 | Fold at high cell density and pH <7 | Fold at low cell density and pH >7.4 |
|---|---|---|---|---|
| DU145 | 12.921 ± 2.39 | 11.192 ± 1.149 | ~1.0 | 13.7 |
| PC3 | 3.854 ± 0.149 | 7.463 ± 0.308 | 1.94 | 16.5 |

Example 10: Cytotoxicity of Emetine and Dithiocarbamate Salt

Studies were carried out on three prostate cancer cell lines: LNCaP, PC3, and DU145. The $IC_{50}$ of emetine after a 3 day exposure was 32.9 nM in LNCaP, 35.1 nM in PC3, and 37.9 nM in DU145, and after a seven day exposure, the values were 31.6, 29.4, and 23.4 nM, respectively. There was not a significant difference in cytotoxicity of emetine between days 3 and 7. However, for the dithiocarbamate salt (Compound 2), in vitro studies revealed an $IC_{50}$ of 564.9 nM in LNCaP (about 17.2 fold reduction compared to emetine), 442.0 nM in PC3 (about 12.6 fold) and 376.8 nM in DU145 (about 9.9 fold) after a 3 day exposure. A gradual increase in activity was seen as exposure to the drug progressed to day 7 and $IC_{50}$ values of 79.0, 87.1, and 79.3 nM respectively, was observed. This increase is most likely due to the release of emetine from the dithiocarbamate salt over the time period. Further drug release studies at pH 5 confirmed about 45% release of emetine from the dithiocarbamate salt after 3-day incubation at this acidic pH maintained at 37° C., whereas release of emetine from the dithiocarbamate salt was not observed at physiological pH (e.g., about 7.4).

Example 11: Cytotoxicity of Various Compounds of Examples 1-5

Various compounds prepared according to Examples 1-5 were studied in LNCaP, PC3, and DU145 cells. The $IC_{50}$ was determined at 7 days and the results are presented in Table 2 below.

TABLE 2

| | $IC_{50}$ in μM after 7 days | | |
|---|---|---|---|
| COMPOUNDS | LNCaP | PC3 | DU145 |
| Emetine | 0.0278 ± 0.00384 | 0.0268 ± 0.00228 | 0.0237 ± 0.00122 |
| 1 | 0.079 ± 0.00341 | 0.0871 ± 0.00499 | 0.0793 ± 0.00247 |
| 4b | >10 | 6.562 ± 1.113 | >10 |
| 4c | 1.656 ± 0.564 | 2.706 ± 0.192 | 2.467 ± 0.263 |
| 4d | | 2.77 ± 0.06 | 3.05 ± 0.07 |
| 4f | 1.97 ± 0.088 | 1.56 ± 0.29 | 1.98 ± 0.213 |
| 4g | 1.698 ± 0.187 | 2.768 ± 0.146 | 2.795 ± 0.151 |
| 4h | 1.613 ± 0.066 | 3.027 ± 0.16 | 2.3 ± 0.067 |
| 4i | | 2.692 ± 0.145 | 2.449 ± 0.162 |
| 4l | 2.308 ± 0.174 | 4.855 ± 0.153 | 2.253 ± 0.084 |
| 5b | 2.1622 ± 0.122 | | |
| 8b | 2.097 ± 0.284 | 4.012 ± 0.868 | |
| 8e | 2.263 ± 0.798 | >10.0 | >10.0 |
| 8a | | | 6.241 ± 0.098 |
| 8d | | 4.214 ± 0.435 | 6.619 ± 0.167 |
| 8c | | 4.576 ± 0.383 | 8.038 ± 0.06 |
| 8f | | 6.075 ± 0.105 | |
| 11a | | 0.484 ± 0.0247 | |
| 11b | | | 0.467 ± 0.025 |
| 11c | | 0.505 ± 0.0159 | |
| 11d | 0.339 ± 0.0327 | 0.443 ± 0.0383 | |
| 11e | 2.057 ± 0.438 | 6.916 ± 0.0711 | 1.535 ± 0.254 |
| 11g | 1.59 ± 0.151 | 2.864 ± 0.0662 | 2.32 ± 0.091 |
| 11h | | | 2.366 ± 0.112 |
| 11f | | 5.002 ± 0.307 | |
| 11j | | | 2.627 ± 0.106 |
| 11i | | 5.271 ± 0.372 | |
| 11k | 1.313 ± 0.166 | 6.915 ± 0.170 | 6.587 ± 0.0348 |
| 11l | 1.700 ± 0.144 | 2.454 ± 0.323 | |
| 11m | 1.006 ± 0.249 | 1.425 ± 0.336 | |
| 11n | | >10 | |
| 13e | 2.115 ± 0.576 | | |

Example 12: Cytotoxicity of Compounds of Example 6

Various compounds prepared according to Example 6 were studied in DU145 and PC3 cells. The $IC_{50}$ was determined at 3, 5, and 7 days. The results are presented in Tables 3 and 4 below.

TABLE 3

| | $IC_{50}$ in μM in DU145 | | |
|---|---|---|---|
| COMPOUNDS | Day 3 | Day 5 | Day 7 |
| 15a2 | 7.9611 ± 0.3119 | 5.7299 ± 0.1819 | 4.2273 ± 0.4183 |
| 15b2 | 6.5257 ± 0.0852 | 5.9855 ± 0.2385 | 5.2184 ± 0.0459 |
| 15c2 | 0.2477 ± 0.0418 | 0.09413 ± 0.00211 | 0.08454 ± 0.00474 |
| 15d2 | 2.5764 ± 0.1905 | 2.0127 ± 0.0734 | 1.792 ± 0.1339 |
| 15e2 | 0.7331 ± 0.022 | 0.6408 ± 0.0543 | 0.8019 ± 0.0198 |

TABLE 4

| | $IC_{50}$ in μM in PC3 | | |
|---|---|---|---|
| COMPOUNDS | Day 3 | Day 5 | Day 7 |
| 15a2 | 8.3891 ± 0.2083 | 7.0582 ± 0.01566 | 7.7083 ± 0.1507 |
| 15b2 | 7.5793 ± 0.1350 | 5.9855 ± 0.2385 | 7.5141 ± 0.1677 |
| 15c2 | 0.5282 ± 0.0237 | 0.4239 ± 0.00785 | 0.4865 ± 0.0688 |
| 15d2 | 3.0639 ± 0.1105 | 2.426 ± 0.1183 | 2.8886 ± 0.1233 |
| 15e2 | 2.495 ± 0.0722 | 1.818 ± 0.1613 | 2.149 ± 0.131 |

Example 13: Evaluation of pH-Responsiveness of Compounds by HPLC

Relative rates of hydrolysis of the compounds listed in Table 5 below over a 48 hour period were evaluated using the percent emetine released from the acid catalyzed hydrolysis of compounds 1 to 6.

TABLE 5 pH Activated Emetine Analogs

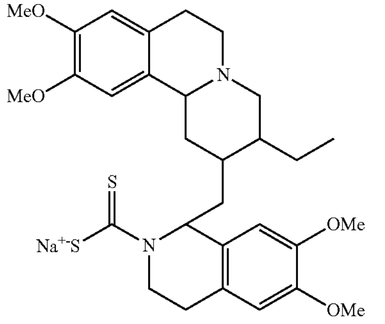

1

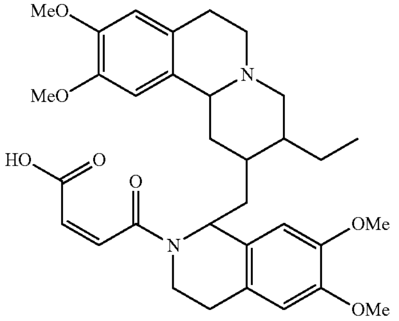 [SMILES: CCC1CN2CCc3cc(OC)c(OC)cc3C2CC1CC1c2cc(OC)c(OC)cc2CCN1C(=O)/C=C\C(=O)O]

2

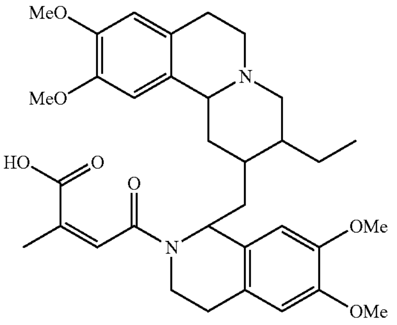 [SMILES: CCC1CN2CCc3cc(OC)c(OC)cc3C2CC1CC1c2cc(OC)c(OC)cc2CCN1C(=O)/C=C(/C)C(=O)O]

3

TABLE 5-continued pH Activated Emetine Analogs

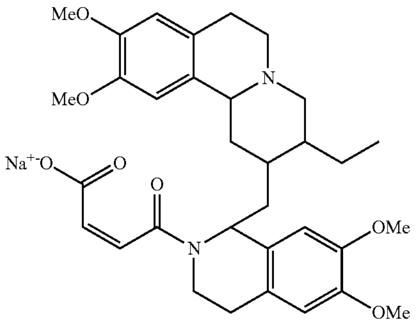

4

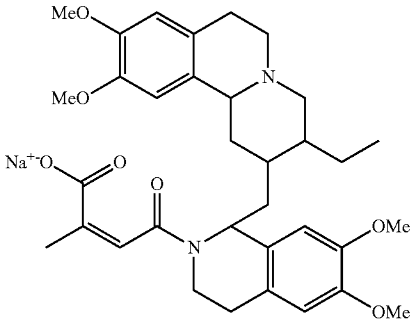

5

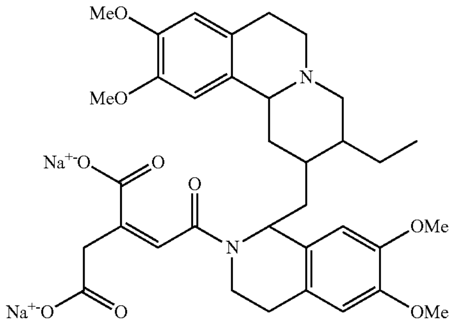

6

The compounds were incubated in aqueous phosphate buffer at pH 5.5, 6.5 and 7.4 at 37° C. over a 48 hour period. High performance liquid chromatography (HPLC) was employed to analyze the samples and quantify how much emetine was released. The data is summarized in Table 5 below. The compounds whose hydrolysis to emetine is shown in table 5 are all 100% stable at physiological pH 7.4 up to a 5 day exposure. All the compounds studied here were activated to emetine at pH 5.5 over a 48 hour period, although to different extents. Percent hydrolysis to emetine was found to drop at the less acidic pH 6.5.

The rates of hydrolysis of the sodium salts 4-6 and the free acid 2 and 3 are similar to that of maleic anhydride derivatives. Hence, amide analogues synthesized from maleic anhydride and its derivatives in this study showed great promise as seen particularly in compounds 2, 3 and 5 which release about 50%, 80% and 50% emetine, respectively, within 48 hours at pH 6.5. In addition, the free acid analogs 2 and 3 appear to be more pH-responsive and sensitive than the corresponding sodium carboxylate salts 4 and 5, respectively. The pH responsiveness of the sodium dithiocarbamate salt 1 is higher at pH 5.5 than at 6.5 producing about 94.5% hydrolysis within 48 hours at pH 5.5, but only 13.2% over the same period at pH 6.5. The hydrolysis of 1 appears to be slower at pH 6.5 and it is therefore conceivable that there is an increase in amount of emetine released between day 3 and day 5 in the in vitro study, thereby showing that the compound likely has optimum activity by day 5.

TABLE 5 pH-responsiveness of emetine pro-drugs 1 to 6 in aqueous solutions of pH 5.5 and 6.5; and stability in aqueous solutions of pH 7.4 to 8.0

| | % Emetine* at pH 5.5 | | | % Emetine* at pH 6.5 | | | % Emetine* at pH 7.4 to 8.0 over 72 hrs | | |
|---|---|---|---|---|---|---|---|---|---|
| Compounds | 0 hr | 24 hrs | 48 hrs | 0 hr | 24 hrs | 48 hrs | 0 hrs | 24 hrs | 48 hrs |
| 1 | 0.0% | 55.9% | 94.5% | 0.0% | 5.2% | 13.2% | 0.0% | 0.0% | 0.0% |
| 2 | 0.0% | 36.3 | 54.10 | 0.0% | 35.5% | 52.1% | 0.0% | 0.0% | 0.0% |
| 3 | 0.0% | 78.1 | 93.4 | 0.0% | 76.8% | 82.7% | 0.0% | 0.0% | 0.0% |
| 4 | 0.0% | 19.2% | 27.1% | 0.0% | 8.2% | 17.1% | 0.0% | 0.0% | 0.0% |
| 5 | 0.0% | 61.5% | 77.3% | 0.0% | 24.9% | 49.2% | 0.0% | 0.0% | 0.0% |
| 6 | 0.0% | 33.9% | 42.1% | 0.0% | 13.4% | 21.1% | 0.0% | 0.0% | 0.0% |

*% Emetine = Percent composition of emetine in the mixture due to acid initiated hydrolysis at different time points after incubation at 37° C.

Example 14: In Vitro Cytotoxic Studies of Compounds 1 and 5 in PC3 Cell Line Under Pre-Established Acidic Cancer Cell Culture Medium (pH<7.0)

Figure 3:
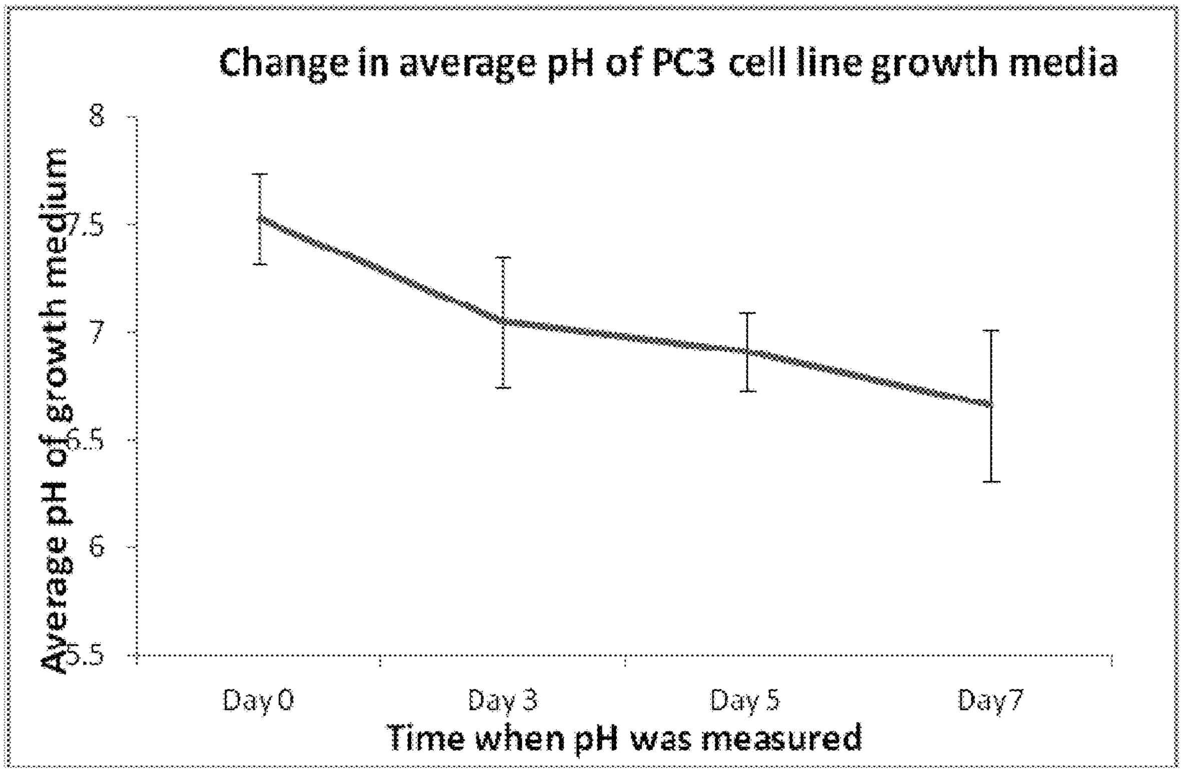
FIG. 3 includes a chart showing reduction of average growth medium over seven days due to the metabolism of PC3 prostate cancer lines.

Upon establishing the release of emetine from these compounds under mildly acidic condition, it was believed that the potency of the pH-responsive analogs could be increased if the cancer cell was adapted to an acidic medium, so that the pH of the cell culture is already below 7 at day 0. To investigate this, compounds 1 and 5, which are two of the three most cytotoxic pH-responsive analogs, were selected. The range of pH changes of the PC3 cell lines in the in vitro studies over a 7 day period was established. The effects of the metabolism of PC3 cell lines on change in pH of growth medium without any drugs was investigated and the results are presented in FIG. 3. This study showed that the metabolic activities of the PC3 cancer cells cause a fall in the pH of the growth medium from 7.4 on day 0 to 7.05 on day 3 and 6.66 by day 7.

In the initial in vitro cytotoxic studies on these compounds, a gradual reduction in the pH of the growth medium was observed as the cancer cells metabolized over a seven day period. Therefore, it was believed to be possible to adapt the prostate cancer cells to low pH between 6.5 and 7.0. Hence, confluent PC3 cell lines were left incubated at 37° C. until the growth medium attained a low pH of 6.7-7.0. The cells were further passaged twice into RPMI medium (pH 6.7-7.0) to allow them adapt to this low pH environment. These cancer cells were then suspended in growth media buffered at pH 6.8 using $KH_2PO_4$, and plated in a 96 well plate. The cell suspension was made at a density of 2000 cells per 100 μL and then plated in a 96 well plate at a density of 2000 cells/well. Cells from the same passage were also plated in normal RPMI growth medium of pH 7.4. The growth of PC3 cell lines under these two pH conditions was monitored over a 5-day incubation period.

Figure 4:
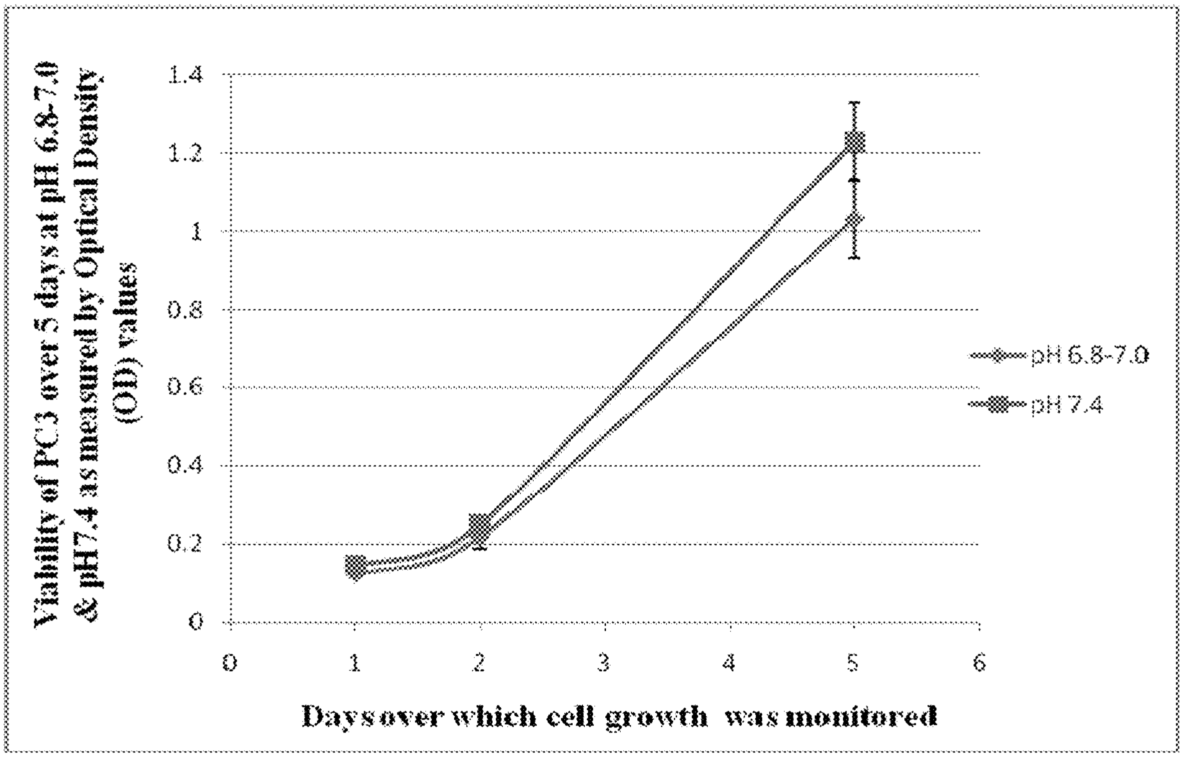
FIG. 4 includes a chart comparing growth of PC3 cell lines in growth medium of pH 6.8-7.0 and pH 7.4.

MTT cell proliferation assay was done on each of day 1, day 2 and day 5. Growth of cells under these two conditions is comparable. Medium was drawn off the wells on day 0, day 3, day 5 and day 7 of incubation. pH was measured and average pH calculated. They both gave a comparable growth curve as shown as FIG. 4.

Cells were incubated for 48 hours to give room for metabolism that might lead to further lowering of pH before drug treatment. Cells were then treated with six different concentrations of each drug (1 or 5) prepared in a growth medium of pH 6.8. Emetine dihydrochloride was used as a positive control. Due to cancer cell metabolism, the average pH gradually decreased further to as low as 6.4 by the fifth day of this study.

In vitro activation of pH-responsive representative emetine prodrug 1 and 5 was analyzed by measuring the change in ratio of cytotoxic $IC_{50}$ values of each drug compared to that of emetine on day 5 in PC3 cell lines under different pH conditions. As expected, the difference in the cytotoxicity of 1 and 5 compared to that of emetine reduced drastically (only about 2 fold difference from emetine) at pH<7.0. On the other hand, there is more than 16 fold difference in the cytotoxicity of 1 and 5 relative to emetine at pH 7.4, as shown in Table 6 below. The increased cytotoxicity of these prodrugs (1 and 5) at pH less than 7.0 is thus in agreement with their activation to emetine under slightly acidic environment. Hence, it appears that emetine is the major cytotoxic agent when these compounds are subject to pH<7.0. In addition, the results at pH 7.4 compared to pH<7.0 indicate that these compounds are far more activatable in the acidic cancer environment thus establishing these compounds as potential prodrugs of emetine.

This became the in vitro model for performing a pH-responsive prodrug activation assay.

TABLE 6

| Compound | $IC_{50}$ fold at pH 7.4[a] | $IC_{50}$ fold at pH <7.0[a] |
|---|---|---|
| 1 | 16.5 | 1.9 |
| 5 | 16.8 | 2.5 |

[a]$IC_{50}$ fold at each pH is determined as: $IC_{50}$ of each drug/$IC_{50}$ of emetine.

These results suggest that an appropriately designed emetine analog could become a valuable cancer chemotherapy. The vital role of the N2' secondary amine is seen in the reduced cytotoxicity of all the N2' derived analogs. These analogs can be hydrolyzed to emetine at variable rates that depends on the substituent at the "tunable handle." It is also vital to note that these compounds are relatively stable at pH 7.4, indicating that emetine will most likely not be released in the blood or the environment of normal tissue.

Example 15: In Vivo Toxicity Study

Each experiment or dosage involved three mice, and drug solutions were made in 1% DMSO/PBS. Each experiment was done three times. A single dose of emetine at 100 MPK (milligrams per kilogram) killed all three mice within 48 hours, while 33 and 11 MPK caused slight weight loss.

Two prodrug compounds were also tested. The tested compounds were labeled "compound 1" and "compound 5" and are identified in the table below.

Compound 1

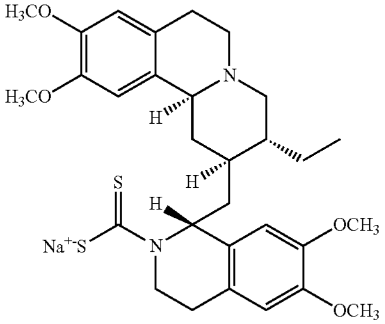

-continued

Compound 5

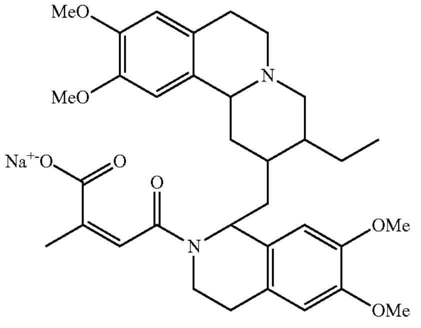

5

The compounds were subjected to in vivo toxicity studies as follows. Compound 1 and Compound 5 in mice produced no noticeable toxicity at 100 MPK or below (33 and 11 MPK). This observation was the same on the third and fourth day. On day 5, no noticeable toxicity effect was seen in mice receiving compound 1 and compound 5 at 11 and 33 MPK, but a slight weight loss was observed in those receiving these two drugs at 100 MPK.

While the invention has been described in terms of preferred embodiments, those skilled in the art will recognize that the invention can be practiced with modification within the spirit and scope of the appended claims.

The instant application contains a Sequence Listing which has been submitted via EFS-Web in an ASCII text file labeled 8823-130777-US and is hereby incorporated by reference in its entirety.

What is claimed:

1. A compound of formula (I):

Formula (I)

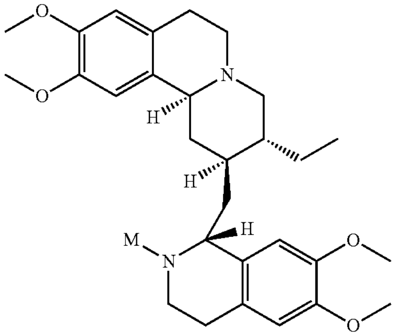

where M is selected from the group consisting of:

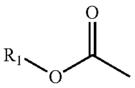, 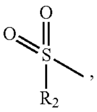, 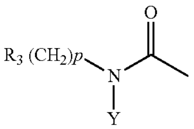, 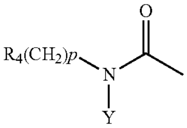, 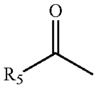, 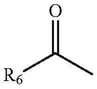, and 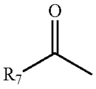, and where:

R1=

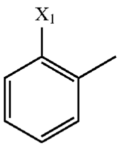

R2=

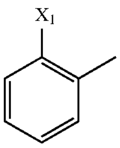

or C1-C4 alkyl,

R3=

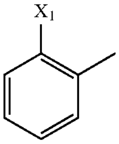 or 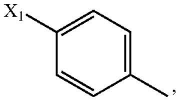,

R4=

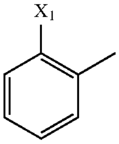 or 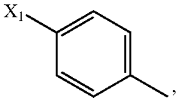,

R5=

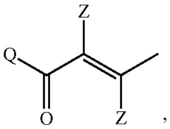,

R6=

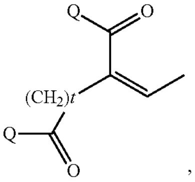,

R7=

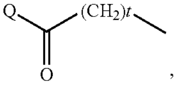, $X_1$=H, —$NO_2$, —$CO_2X_2$, —$OX_3$, halogen, or C1-C4 alkyl, $X_2$=C1-C4 alkyl or H, $X_3$=C1-C4 alkyl or H, Q=–OH or $V^{+-}O$—, V=metal ion, Y=H or C1-C6 alkyl, Z=H, C1-C4 alkyl, or halogen, p=0 to 8, and t=1 to 4.

2. A pharmaceutical composition comprising:

a prodrug comprising a compound of claim 1; and a pharmaceutically acceptable carrier.

3. A method of delivering emetine to a subject comprising administering to the subject an effective amount of a compound according to claim 1.

4. A method of treating breast cancer, leukemia, lung cancer or prostate cancer in a subject, the method comprising administering a compound according to claim 1 to a subject having metastatic or non-metastatic cancer.

5. The method of claim 4, wherein the cancer is prostate cancer or breast cancer.

6. A method for decreasing the toxicity of emetine, the method comprising synthesizing a prodrug comprising a compound according to claim 1, wherein the compound is hydrolyzed at a pH of less than about 7.0.

7. The method according to claim 6, wherein the compound is hydrolyzed at a pH of less than about 6.9.

8. The method according to claim 6, wherein the compound is hydrolyzed at a pH of less than about 6.8.

* * * * *